US008771723B2

(12) United States Patent
Perdok et al.

(10) Patent No.: US 8,771,723 B2
(45) Date of Patent: Jul. 8, 2014

(54) COMPOSITIONS FOR REDUCING GASTRO-INTESTINAL METHANOGENESIS IN RUMINANTS

(76) Inventors: Hindrik Bene Perdok, Velddriel (NL); Sander Martijn Van Zijderveld, Velddriel (NL); John Richard Newbold, Velddriel (NL); Rob Bernard Anton Hulshof, Velddriel (NL); David Deswysen, Velddriel (NL); Walter Jan Jozef Gerrits, Renkum (NL); Jan Dijkstra, Wageningen (NL); Ronald Alfred Leng, Yandina Creek (AU)

( * ) Notice: Subject to any disclaimer, the term of this patent is extended or adjusted under 35 U.S.C. 154(b) by 0 days.

(21) Appl. No.: 13/386,368

(22) PCT Filed: Jul. 23, 2010

(86) PCT No.: PCT/NL2010/050473
§ 371 (c)(1),
(2), (4) Date: May 14, 2012

(87) PCT Pub. No.: WO2011/010921
PCT Pub. Date: Jan. 27, 2011

(65) Prior Publication Data
US 2012/0219527 A1   Aug. 30, 2012

(30) Foreign Application Priority Data

Jul. 23, 2009  (EP) .................................... 09166276

(51) Int. Cl.
*A23K 1/18* (2006.01)
*A01N 59/02* (2006.01)
*A01N 59/00* (2006.01)
*A01N 63/00* (2006.01)

(52) U.S. Cl.
USPC .......... 424/438; 424/709; 424/718; 424/93.1; 424/93.4

(58) Field of Classification Search
USPC ........................ 424/438, 709, 718, 93.1, 93.4
See application file for complete search history.

(56) References Cited

U.S. PATENT DOCUMENTS

| 3,282,674 A * | 11/1966 | Mohr et al. ................. 71/64.06 |
| 3,753,723 A * | 8/1973 | Henderson et al. ............. 426/49 |
| 3,873,728 A * | 3/1975 | Moore .............................. 426/2 |
| 5,648,258 A * | 7/1997 | Odom ........................ 435/252.1 |
| 5,843,498 A | 12/1998 | Takahashi |
| 6,120,810 A | 9/2000 | Rehberger et al. |
| 6,899,913 B1 * | 5/2005 | Buwalda et al. .............. 426/578 |
| 7,427,397 B2 * | 9/2008 | Adams et al. ................ 424/93.4 |
| 2003/0219437 A1 * | 11/2003 | Yellin et al. ................ 424/144.1 |

FOREIGN PATENT DOCUMENTS

EP  1 630 226 A2  3/2006
WO  WO2011/010921  1/2011

OTHER PUBLICATIONS

Leng RA (05/302009). The Potential of Feeding Nitrate to Reduce Enteric Methane Production in Ruminants. A Report, the Dept. of Climate Change, Commonweath Gov't of Australia. 82pp.*
Screen Capture—Wayback Machine (http://www.archive.org), dating Reference U (Leng) to at least May 30, 2009.*
Siddiqi et al. (1992). Increased exposure to dietary amines and nitrate in a population at high risk of oesophageal and gastric cancer in Kashmir (India). Carcinogenesis, v13(8), p. 1331-1335.*
Kurilich AC et al. (1999). Carotene, Tocopherol, and Ascorbate Contents in Subspecies of *Brassica oleracea*. J Agric Food Chem, v47(4), p. 1576-1581.*
Leng RA (2008 or 2009). The potential of feeding nitrate to reduce enteric methane production in ruminants. Dept of Climate change, Commonweath Gov't of Austrailia, 90 pages.*
Allen D. Tillman et al., "Nitrate Reduction Studies with Sheep", Journal of Animal Science, No. 24, 1965, pp. 1140-1146, XP-002556351.
R. A. Leng, "The Potential of Feeding Nitrate to Reduce Enteric Methane Production in Ruminants", A Report—The Department of Climate Change, Common Wealth Government of Australia, Canberra ACT, Australia, Nov. 2008, XP-002556354.
R.J. Dewhurst et al., "Effect of dietary sulphur sources on concentrations of hydrogen sulphide in the rumen head-space gas of dairy cows", Animal, No. 1, 2007, pp. 531-535, XP-002556353.
R.R. Oltjen et al., "Purified Diet Studies with Sheep", Journal of Animal Science, No. 21, 1962, pp. 277-283, XP-002556352.
Search Report in International Application No. PCT/NL2010/050473 mailed Feb. 25, 2011.
Asanuma et al., "Effect of the Addition of Fumarate on Methane Production by Ruminal Microorganisms In Vitro," J. Dairy Sci. 1999, 82(4):780-787.

(Continued)

*Primary Examiner* — Cherie M Stanfield
*Assistant Examiner* — Sean C Barron

(57) ABSTRACT

The present invention concerns the reduction of gastro-intestinal methanogenesis in ruminants with the aid of agents that compete for the hydrogen atoms required by methanogens during normal fermentation of ingested feed. The invention in one aspect resides in the findings that both nitrate reductive pathways as well as sulphate reductive pathways outcompete gastro-intestinal methanogenesis in ruminants and, that the methanogenesis reducing effects of nitrate and sulphate are completely additive. At the same time the combined administration of nitrate and sulphate was found to be fully effective to avoid or mitigate the potential problems of nitrite intoxication normally encountered when using nitrate alone, which effect is further enhanced, where necessary, by the addition of a nitrite reducing probiotic micoroorganism. Hence, products are provided comprising high amounts of a combination of a nitrate compound and a sulphate compound and optionally a nitrite reducing probiotic microorganism, as well as methods of reducing gastro-intestinal methanogenesis in ruminants using such compositions.

12 Claims, 17 Drawing Sheets

(56) References Cited

OTHER PUBLICATIONS

Beauchemin et al., "Nutritional management for enteric methane abatement: a review," Australian Journal of Experimental Agriculture 2008, 48(2):21-27.

Guo et al., "Use of nitrate-nitrogen as a sole dietary nitrogen source to inhibit ruminal methanogenesis and to improve microbial nitrogen synthesis in vitro," Asian-Australian Journal of Animal Science, 2009, 22(4):542-549.

Iwamato et al., "Effects of nitrate combined with fumarate on methanogenesis, fermentation, and cellulose digestion by mixed ruminal microbes in vitro," Animal Science Journal 1999, 70(6):471-478.

Iwamoto et al, "Effects of pH and electron donors on nitrate and nitrite reduction in ruminal microbiotica," Animal Science Journal, 1999, 72(2):117-125.

Joblin, "Ruminal acetogens and their potential to lower ruminant methane emissions," Australian Journal of Agricultural Research, 1999, 50(8):1307-1314.

Johnson et al., "Methane emissions from cattle," J Anim Sci, 1995, 73(8):2483-2492.

Le Van et al., "Assessment of Reductive Acetogenesis with Indigenous Ruminal Bacterium Populations and *Acetitomaculum ruminis*," Appl. Environ. Microbiol., 1998, 64(9):3429-3436.

Lewis, "The metabolism of nitrate and nitrite in the sheep; the reduction of nitrate in the rumen of the sheep," Biochem. J., 1951, 48(2):175-170.

Molano et al., "Fumaric acid supplements have no effect on methane emissions per unit of feed intake in wether lambs," Australian Journal of Experimental Agriculture, 2008, 48(2):165-168.

Sar et al., "Effect of *Escherichia coli* wild type or its derivative with high nitrite reductase activity on in vitro ruminal methanogenesis and nitrate/nitrite reduction," J. Anim Sci., 2005, 83(3):644-652.

Sar et al., "Manipulation of rumen methaongensis by the combination of nitrate with [beta]1-4 galacto-oligosaccharides or nisin in sheep," Animal Feed Science and Technology (2004)m 115(1-2):129-142.

Steinfeld et al., "Livestock's Long Shadow," Food and Agriculture Organization of the United Nations, 2006.

Takashi et al., "Inhibitory effects of sulphur compounds, copper and tungsten on nitrate reduction by mixed rumen micro-organisms," British Journal of Nutrition, 1989, 61(03):741-748.

Takashi et al., "Prophylactic effect of L-cysteine on nitrate-induced alterations in respiratory exchange and metabolic rate in sheep," Animal Feed Science and Technology, 1991, 35:105-113.

Takashi et al., "Prophylactic effect of L-cysteine to acute and subclinical nitrate toxicity in sheep," Animal Feed Science and Technology, 1989, 74(3):273-280.

Ungerfeld et al., "A meta-analysis of fumarate effects on methine production in ruminal batch cultures," J. Anim Sci., 2007, 85(10):2556-2563.

Lin et al., "Effects of nitrate adaptation by rumen inocula donors and substrate fiber proportion on in vitro nitrate disappearance, methanogenesis, and rumen fermentation acid". Animal Journal, 2013, 7 pages. Retrieved on line, http://dx.doi.org/10.1017/S1751731113000116.

\* cited by examiner

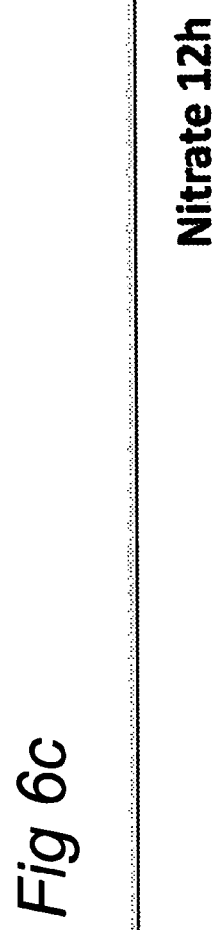

COMPOSITIONS FOR REDUCING GASTRO-INTESTINAL METHANOGENESIS IN RUMINANTS

FIELD OF THE INVENTION

The present invention concerns the field of feed additives and supplements for ruminants. More in particular, the invention concerns the reduction of gastro-intestinal methanogenesis in said ruminants with the aid of inhibitory agents that compete for the hydrogen atoms required by methanogens during normal fermentation of ingested feed. The present invention provides, amongst others, feed supplements and feed compositions comprising said inhibitory agents and their non-therapeutic use for reducing methanogenesis.

BACKGROUND OF THE INVENTION

Methanogenesis is the main route of hydrogen (H2) disposal during the process of rumen fermentation (Beauchemin et al., 2008). Removal of H2 from the rumen milieu is essential for the efficient continuation of rumen fermentation, but the methane resulting from methanogenesis has been implicated both as a loss of dietary energy to the animal (Johnson and Johnson, 1995) as well as a significant greenhouse gas contributing to global warming (Steinfeld et al., 2006). Both subjects have led to a global search for feed additives to mitigate methane production from ruminants.

One of the options explored to reduce methane emissions is the redirection of excess H2 into processes that yield more beneficial products for the ruminant, thereby lowering methanogenesis. Examples include the stimulation of propiogenesis by addition of propionate precursors and attempts to introduce reductive acetogenesis into the rumen (Joblin, 1999, Molano et al., 2008). Successful induction of these processes in the rumen would respectively yield propionate or acetate as nutrients for the animal, while at the same time reducing the availability of H2 for methanogenesis. However, the introduction of propionate precursors (malate and fumarate) has yielded variable effects on methane production (Asanuma et al., 1999, Ungerfeld et al., 2007) and attempts to introduce reductive acetogenesis in the rumen have failed so far because of a lower affinity for hydrogen when compared to methanogenesis (Le Van et al., 1998).

Another options for reducing methane emissions has been described in U.S. Pat. No. 5,843,498, which concerns ruminant feed compositions for depressing rumen methanogenesis and improving feed efficiency comprising, as an effective component, cysteine and/or its salts.

A small number of research groups have looked into the potential of nitrate as methane reducing feed additive, and the addition of nitrate appears to consistently lower methanogenesis (Guo et al., 2009, Sar et al., 2005, Takahashi et al., 1998).

The possibility to introduce nitrate (NO3) as alternative hydrogen sink to reduce methanogenesis in the rumen has been largely ignored, due to consistent findings of toxic effects from nitrite that is formed as an intermediate during the reduction of nitrate to ammonia in the rumen (Lewis, 1951). High doses of nitrate in ruminant diets have been reported to cause methemoglobinemia, reducing the blood's capacity to transport oxygen to the animals' tissues. In addition, nitrite accumulation in the rumen is known to reduce microbial activity in the rumen, which inter alia may reduce feed intake by the animal.

It has been suggested to supplement high nitrate fed ruminants with formate, lactate or fumarate, in order to alleviate the inhibitory effect of nitrite on fermentation (Iwamoto, 1999; Iwamoto, 2001). The simultaneous administration of nitrate and GOS or nisin has also been reported as an effective measure to lower the concentration of rumen and plasma nitrite and methemoglobin, while keeping rumen methanogenesis at a low level, as compared to nitrate treatment alone (Sar, 2004).

Acceleration of nitrite reduction using probiotics has also been the subject of extensive research. U.S. Pat. No. 6,120,810 teaches to decrease ruminant intoxication by nitrates by administering to the animal a composition containing an effective amount of the nitrite reducing microorganism *Propionibacterium acidiproprionici*. European patent application no. 1 630 226 discloses a feed composition for ruminants containing a microbe having nitrite reductase activity, which is selected from intestinal bacteria, coryneform bacteria, *Bacillus subtilis*, bacteria of the genus *Methylophilus, Actinomyces*, ruminal bacteria and combinations thereof. It has also been reported (Sar, 2005) that *E. Coli* W3110 might be used to abate intoxication when nitrate is used to inhibit methanogenesis in ruminants.

Inhibitory effects of sulphur compounds, copper and tungsten on nitrate reduction have been investigated (Takahashi, 1989). The authors report that in rumen fluid from nitrate adapted wethers (0.55 g NaNO3/kg body weight twice daily) nitrite formation was affected neither by incubation with Sulphate-S nor by incubation with sulphite-S. Of the S-containing amino acids, methionine proved to be inefficient in inhibiting microbial reduction of nitrate whereas cystein significantly lowered nitrite formation. This publication did not concern or address any methanogenesis reducing effects. The effectiveness of cystein in preventing nitrite accumulation was confirmed in later studies (Takahashi, 1991; Takahashi 1998).

It is the primary objective of the present invention to provide treatments, and the compositions for use therein to further reduce methanogenesis in ruminants while avoiding or overcoming the particular problems associated with nitrite accumulation.

SUMMARY OF THE INVENTION

The present invention resides, in one aspect, in the findings that both nitrate reductive pathways as well as sulphate reductive pathways outcompete gastro-intestinal methanogenesis in ruminants and, that the methanogenesis reducing effects of nitrate and sulphate obtained when used individually are completely additive, as will be illustrated in detail in the experimental part. The individual effects of nitrate and sulphate appear to be independent.

At the same time the combined administration of nitrate and sulphate was found to be fully effective to avoid or mitigate the potential problems of nitrite intoxication normally encountered when using nitrate alone, as will be illustrated in more detail in the experimental part.

Surprisingly, whereas nitrate administration was found to reduce enteric methanogen counts, administration of sulphate or of a combination of nitrate and sulphate does not. Administering the combination of nitrate and sulphate does however significantly reduce the proportion of methanogens of the total bacteria.

Although the scope of the invention is not limited to or reduced by any such underlying theory or hypothesis, it is believed that the reduction of methanogenesis (equation 1) by nitrate is caused by the alternative use of $H_2$ in the reduction of nitrate to ammonia. Nitrate reduction in the rumen is believed to follow the reduction pathway described in equation 2. This implies that 8 moles of H are redirected towards nitrate reduction, thereby theoretically reducing methane production with 1 mole for each mole of nitrate fed. Each 100 g of NO3 fed would in this way lead to a $CH_4$-reduction of 25.8 g.

$$CO_2 + 4H_2 \rightarrow CH_4 + 2H_2O \quad \text{(equation 1)}$$

$$NO_3^- + 4H_2 + 2H^+ \rightarrow NH_4^+ + 3H_2O \quad \text{(equation 2)}$$

The reduction of nitrate to ammonia yields more energy than the reduction of $CO_2$ to $CH_4$, and could thus be expected to be the principal route of $H_2$-disposal if sufficient nitrate is available in the rumen. The full reduction of $NO_3$ to $NH_3$ consumes 8 electrons and each mole of nitrate reduced could thus lower methane emissions by 1 mole of methane. The end product of the reaction, ammonia, can be considered a valuable nutrient for ruminants fed low protein diets.

As noted above, the present inventors found that sulphate itself is also a strong reductant effective in reducing methane emissions by a mechanism independent of the nitrate reduction. Sulphate reduction to $H_2S$ (equation 3) also consumes 8 electrons and thus offers the same potential to reduce methane emissions as nitrate per mole.

$$SO_4^{2-} + 4H_2 + 2H^+ \rightarrow H_2S + 4H_2O \quad \text{(equation 3)}$$

The finding that sulphate is also effective in reducing methanogenesis may be explained from the fact that, from a thermodynamic perspective, sulphate reduction is also likely to be more favourable than methanogenesis. Stochiometrically, the full reduction of 100 g sulphate to hydrogen sulphide would reduce $CH_4$-production by 16.7 g.

Hydrogen sulphide ($H_2S$) appears to play a role as electron donor in the reduction of $NO_2$ to $NH_4^+$, and supplementation of the diet with sulphate may therefore additionally cause the alleviation in nitrite accumulation in the rumen.

It was furthermore found that results can be enhanced even further by the additional administration of an effective amount of nitrite reducing probiotic microorganisms. As will be illustrated in detail in the experimental part, an initial delay is observed in the onset of nitrite reduction by sulphate, which may be explained by a delay in $H_2S$ availability immediately after feed intake. This may in turn cause a reduction in feed intake, and it is therefore a further object of the invention to avoid this. The inventors found that this could be realized by the co-administration of certain nitrite reducing probiotic microorganisms as will be illustrated in more detail in the experimental part.

DETAILED DESCRIPTION OF THE INVENTION

Figure 1:
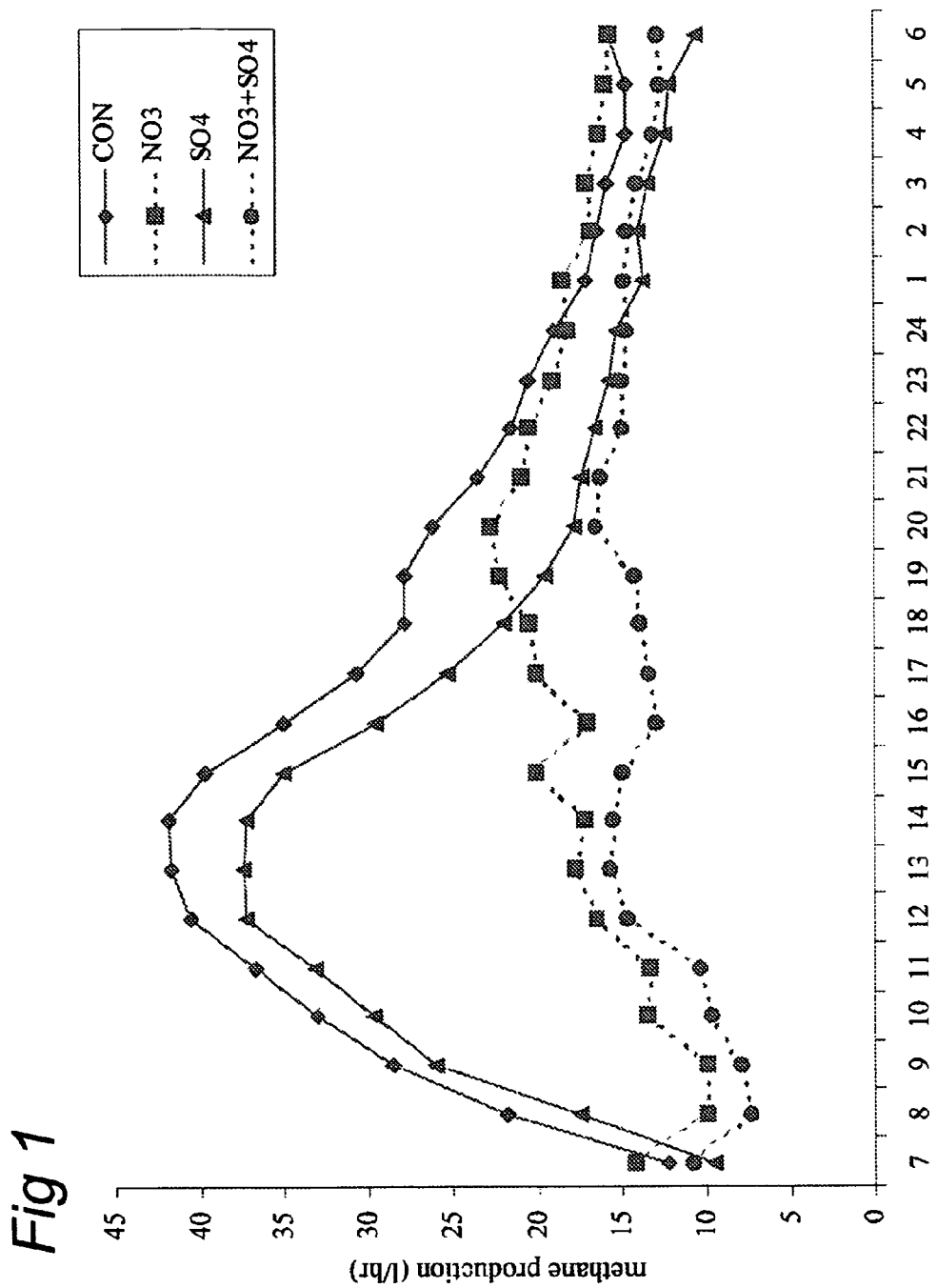
FIG. 1 is a graph showing the methane production (1/hr) over the course of a 24 period in male Texel cross lambs receiving either a basal diet or one of three experimental diets, which were supplemented with a nitrate compound, a sulphate compound or a combination of a nitrate compound and a sulphate compound.

A first aspect of the invention concerns an animal feed supplement comprising 10-100% of a combination of a nitrate compound and a sulphate compound.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

As used, herein the term "animal feed supplement" refers to a concentrated additive premix comprising the active ingredients, which premix or supplement may be added to an animal's feed or ration to form a supplemented feed in accordance with the present invention. The terms "animal feed premix," "animal feed supplement," and "animal feed additive" are generally considered to have similar or identical meanings and are generally considered interchangeable. Typically, the animal feed supplement of the present invention is in the form of a powder or compacted or granulated solid. In practice, livestock may typically be fed the animal feed supplement by adding it directly to the ration, e.g. as a so-called top-dress, or it may be used in the preparation or manufacture of products such as compounded animal feeds or a lick blocks, which will be described in more detail hereafter. The invention is not particularly limited in this respect. A supplement, according to the invention is typically fed to an animal in an amount ranging from 16-2500 g/animal/day.

The present animal feed supplement comprises a nitrate compound, typically a physiologically acceptable or tolerated nitrate compound. In accordance with the invention, the nitrate-N needs to be readily available for reduction by rumen or gut microorganisms and the nitrate compound should have sufficient solubility in water. Hence, in accordance with this invention the nitrate compound is preferably an ionic nitrate compound, most preferably an inorganic nitrate salt, such as sodium nitrate, potassium nitrate, calcium nitrate, ammonium nitrate, all of which are readily soluble in water at standard temperature and pressure. Furthermore, from a health and safety perspective, it is typically preferred to use complex inorganic nitrate salts, such as the compound represented by the formula $5.Ca(NO_3)_2.NH_4NO_3.10H_2O$, which is commercially available from Yara under the trade name 'Calcinit'.

The present animal feed supplement also comprises a sulphate compound, typically a physiologically acceptable or tolerated sulphate compound. In accordance with the invention It is preferred that the sulphate compound is an ionic sulphate compound, most preferably selected from the group of inorganic sulphate salts, of which many are are highly soluble in water. Exceptions include calcium sulphate. It is particularly preferred that the present sulphate compound is selected from the group of soluble inorganic sulphate salts, including sodium sulphate, potassium sulphate, magnesium sulphate, zinc sulphate, manganese sulphate, copper sulphate and ferrous sulphate.

In preferred embodiments of the invention, the supplement comprises the combination of the nitrate compound and the sulphate compound in an amount ranging from 10-100 wt %, preferably said amount is in excess of 10, 20, 30, 40, 50, 60, 70, 80, 90, 95, 97 or 99 wt %, on a dry weight basis.

Since the present invention in part resides in the finding that, for the purpose of reducing gastrointestinal methanogenesis in the ruminant, nitrate and sulphate are in part interchangeable, the molar ratio between nitrate and sulphate in the supplement can typically range from 100:1-1:50, more preferably from 50:1-1:10, 25:1-1:5, or 10:1-1:2.5, and most preferably 5:1-1:1.

The combination of nitrate compound and sulphate compound in the feed supplement of the invention typically provide a total amount of nitrate and sulphate in excess of 50 g/kg, on a dry weight basis. In a preferred embodiment said total amount of nitrate and sulphate exceeds 75 g/kg, more preferably 90 g/kg, most preferably 100 g/kg. In practice said amount typically is below 750 g/kg. In another preferred embodiment, the amount of sulphate in the feed supplement exceeds 25 g/kg, more preferably 40 g/kg, most preferably 50 g/kg, on a dry weight basis. Typically said amount does not exceed 250 g/kg, preferably it does not exceed 200 g/kg, most preferably it does not exceed 165 g/kg. In another preferred embodiment, the amount of nitrate in the feed supplement exceeds 20 g/kg, more preferably 30 g/kg, most preferably 40 g/kg, on a dry weight basis. Typically said amount is below 600 g/kg, more preferably below 550 g/kg, on a dry weight basis.

All the amounts and/or dosages of 'nitrate' and/or 'sulphate' as used herein, unless indicated otherwise, refer to the weight of nitrate and/or sulphate comprised in or provided by the nitrate and/or sulphate compounds, relative to total dry weight of the composition, as will be understood by those skilled in the art. It is within the skills of the trained professional to determine exactly the ideal amounts of the components to be included in the supplement and the amounts of the supplement to be used in the preparation of the ration or compounded animal feed, etc., taking into account the specific type of animal and the circumstances under which it is held. Preferred dosages of each of the components are given below.

The animal feed supplements of the present invention may comprise any further ingredient without departing from the scope of the invention. It may typically comprise well-known excipients that are necessary to prepare the desired product form and it may comprise further additives aimed at improving the quality of the feed and/or at improving the performance of the animal consuming the supplement. Suitable examples of such excipients include carriers or fillers, such as lactose, sucrose, mannitol, starch crystalline cellulose, sodium hydrogen carbonate, sodium chloride and the like and binders, such as gum Arabic, gum tragacanth, sodium alginate, starch, PVP and cellulose derivatives, etc. Examples of feed additives known to those skilled in the art include vitamins, amino acids and trace elements, digestibility enhancers and gut flora stabilizers and the like.

In a preferred embodiment, the animal feed supplement additionally comprises a nitrite reducing probiotic microorganism. As used herein the term 'nitrite probiotic microorganism' refers to live microorganisms which when administered in adequate amounts confers a health benefit on the host, by reducing nitrite accumulating in the rumen and/or gut to ammonium as explained herein before. Many examples of such nitrite reducing microorganisms are known by those skilled in the art. Preferred examples of nitrite reducing probiotic microorganisms include ruminal and intestinal bacteria having nitrite reductase activity, *Propionibacterium acidiproprionici*, coryneform bacteria, *Bacillus subtilis*, bacteria of the genus *Methylophilus, Actinomyces* and *Escherichia coli* W3110. Most preferably, in accordance with the present invention, the nitrite reducing probiotic microorganism is selected from the group of *Megasphaera elsdenii*, in particular ruminal strains thereof, and *Propionibacterium acidipropionici*, in particular *Propionibacterium acidipropionici* strain P5, registered under accession number 55467 in the microorganism collection of the American Type Culture Collection (ATCC) and commercially available as 'Bova-Pro® concentrate' from Agtech Products Inc.

In a preferred embodiment, an animal feed supplement as defined herein before is provided, which additionally comprises said nitrite reducing probiotic microorganism in an amount of $1.0*10^8$-$1.0*10^{14}$ cfu/kg, more preferably $1.0*10^9$-$1.0*10^{13}$ cfu/kg, most preferably $1.0*10^{10}$-$1.0*10^{12}$ cfu/kg, for example $1.0*10^{11}$ cfu/kg, on a dry weight basis. As is known by those skilled in the art the colony-forming unit (CFU) is a measure of viable bacterial or fungal numbers. Unlike in direct microscopic counts where all cells, dead and living, are counted, CFU measures viable cells and is for example determined by expanding a (diluted) sample on an agar or trypticase soy agar plate and counting colonies thus obtained.

Furthermore, the present inventors have found that good results are obtained when lactic acid or a lactate compound is administered. Without wishing to be bound by any particular theory, it is believed that lactic acid or lactate supplementation can enhance the effectiveness of the probiotic microorganisms. Hence, in a preferred embodiment, a compounded animal feed as defined herein before is provided, which additionally comprises an effective amount of lactate or a lactic acid, preferably it comprises lactic acid or lactate in an amount exceeding 20 g/kg, more preferably 30 g/kg, most preferably 40 g/kg, on a dry weight basis.

A further aspect of the invention concerns products such as a compounded animal feeds and a lick blocks, comprising a supplement as defined herein before.

Hence, in an aspect, a compounded animal feed composition is provided comprising a combination of a nitrate compound and a sulphate compound, said combination providing a total amount of nitrate and sulphate in excess of 10 g/kg, on a dry weight basis.

The term 'compounded animal feed composition' as used herein, means a composition which is suitable for use as an animal feed and which is blended from various natural or non-natural base or raw materials and/or additives. Hence, in particular, the term 'compounded' is used herein to distinguish the present animal feed compositions from any naturally occurring raw material. These blends or compounded feeds are formulated according to the specific requirements of the target animal. The main ingredients used in commercially prepared compounded feeds typically include wheat bran, rice bran, corn meal, cereal grains, such as barley, wheat, rye and oat, soybean meal, alfalfa meal, wheat powder and the like. A commercial compound feed will typically comprise no less than 15% of crude protein and no less than 70% digestible total nutrients, although the invention is not particularly limited in this respect. Liquid, solid as well as semi-solid compounded animal feed compositions are encompassed within the scope of the present invention, solid and semi-solid forms being particularly preferred. These compositions are typically manufactured as meal type, pellets or crumbles. In practice, livestock may typically be fed a combination of compounded feed, such as that of the present invention, and silage or hay or the like. Typically a compounded animal feed is fed in an amount within the range of 0.3-10 kg/animal/day. It is within the skills of the trained professional to determine proper amounts of these components to be included in the compounded animal feed, taking into account the type of animal and the circumstances under which it is held.

The combination of nitrate compound and sulphate compound in the compounded animal feed of the invention typically provides a total amount of nitrate and sulphate in excess of 10 g/kg, on a dry weight basis. In a preferred embodiment said total amount of nitrate and sulphate exceeds 15 g/kg, more preferably 17.5 g/kg, most preferably 20 g/kg. In practice said amount typically is below 750 g/kg, preferably below 500 g/kg, more preferably below 250 g/kg. In another preferred embodiment, the amount of sulphate in the compounded animal feed exceeds 5 g/kg, more preferably 7.5 g/kg, 10 g/kg, or 12 g/kg, on a dry weight basis. Typically said amount does not exceed 200 g/kg, preferably it does not exceed 175 g/kg, most preferably it does not exceed 150 g/kg. In another preferred embodiment, the amount of nitrate in the compounded animal feed exceeds 5 g/kg, more preferably 7.5 g/kg, most preferably 10 g/kg, on a dry weight basis. Typically said amount is below 600 g/kg, more preferably below 500 g/kg, most preferably below 250 g/kg, on a dry weight basis. Furthermore, in a preferred embodiment, a compounded animal feed as defined herein before is provided, which additionally comprises the nitrite reducing probiotic microorganism in an amount of $1.0*10^8$-$1.0*10^{14}$ cfu/kg, more preferably $1.0*10^9$-$1.0*10^{13}$ cfu/kg, most preferably $1.0*10^{10}$-$1.0*10^{12}$ cfu/kg. Furthermore, in a preferred embodiment, a compounded animal feed as defined herein before is provided, which additionally comprises an effective amount of lactate or lactic acid, preferably in an amount exceeding 5 g/kg, more preferably 7.5 g/kg, most preferably 10 g/kg.

The compounded animal feed compositions of the invention may comprise any further feed additive typically used in the art. As is known by those skilled in the art, the term 'feed additive' in this context refers to products used in animal nutrition for purposes of improving the quality of feed and the quality of food from animal origin, or to improve the animals' performance, e.g. providing enhanced digestibility of the feed materials. Non-limiting examples include technological additives such as preservatives, antioxidants, emulsifiers, stabilising agents, acidity regulators and silage additives; sensory additives, especially flavours and colorants; (further) nutritional additives, such as vitamins, amino acids and trace elements; and (further) zootechnical additives, such as digestibility enhancers and gut flora stabilizers.

As will be clear to those skilled in the art, the present compounded animal feed compositions can comprise any further ingredient or additive, without departing from the scope of the invention.

In a further aspect, the invention provides a lick stone or lick block comprising the supplement of the invention. As is known to those skilled in the art such lick stones or blocks are particularly convenient for feeding mineral supplements (as well as proteins and carbohydrates) to ruminants grazing either or both natural and cultivated pastures. Such lick blocks or lick stones in accordance with the present invention typically comprise, in addition to the combination of nitrate compound and sulphate compound and the optional nitrite reducing probiotic microorganism of the invention, various types of binders, e.g. cements, gypsum, lime, calcium phosphate, carbonate, and/or gelatin; and optionally further additives such as vitamins, trace elements, mineral salts, sensory additives, etc.

The combination of nitrate compound and sulphate compound in the lick block of the invention typically provides a total amount of nitrate and sulphate in excess of 15 g/kg, on a dry weight basis. In a preferred embodiment said total amount of nitrate and sulphate exceeds 25 g/kg, more preferably 30 g/kg. In practice said amount typically is below 450 g/kg, preferably below 400 g/kg. In another preferred embodiment, the amount of sulphate in the lick block exceeds 3 g/kg, more preferably 5 g/kg, most preferably 6 g/kg, on a dry weight basis. Typically said amount does not exceed 150 g/kg, preferably it does not exceed 100 g/kg, most preferably it does not exceed 75 g/kg. In another preferred embodiment, the amount of nitrate in the lick block exceeds 10 g/kg, more preferably 20 g/kg, most preferably 25 g/kg, on a dry weight basis. Typically said amount is below 400 g/kg, more preferably below 300 g/kg, on a dry weight basis. In a preferred embodiment, an lick block as defined herein before is provided, which additionally comprises the nitrite reducing probiotic microorganism in an amount of $1.0*10^8$-$1.0*10^{14}$ cfu/kg, more preferably $1.0*10^9$-$1.0*10^{13}$ cfu/kg, most preferably $1.0*10^{13}$-$1.0*10^{12}$ cfu/kg.

A further aspect of the invention concerns a method of reducing gastro-intestinal methane production in a ruminant, said method comprising administering to the ruminant an effective amount of a combination of the nitrate compound and the sulphate compound wherein said method is non-therapeutic.

The term 'reducing gastro-intestinal methanogenesis' as used herein refers to the reduction of methane gas production in the gastro-intestinal tract. As explained herein before, fermentation in the rumen and the gut of a ruminant gives rise to production of methane gas by so-called methanogens. The present invention aims to reduce this process, such as to reduce the methane excretion directly from the gastro-intestinal tract. It is within the knowledge and skill of those trained in the art to assess methane excretion by an animal. As explained before, methane production in the rumen and gut is a process normally occurring in healthy animals and decreasing methanogenesis does not enhance or diminish the ruminant's general state of health or well-being. Nevertheless, a reduction of methane formation using the combination of a nitrate compound and a sulphate compound might increase the animal's efficiency of nutrient use, such that the present method might enhance animal growth and/or productivity.

As will be readily recognized by those skilled in the art, the present method of treatment will not be effective in treating a condition known as 'bloat'. Bloat is a condition commonly described as an abnormal distension of the rumen as a consequence of gas accumulation in the rumen. Gas (carbon dioxide, methane and other gases) is normally produced during rumen fermentation and is normally erected through the oesophagus, preventing accumulation of gases. During the incidence of bloat, the oesophagus is blocked by layer of foam. The opening of the oesophagus contains receptors that block the oesophagus if liquid (or foam) is sensed. The foam that is formed during bloat originates from the rapid fermentation of small feed particles. The cause of bloat is the formation of foam and not the production of ruminal gases, which is a naturally occurring process in the ruminant. As a consequence, methane production cannot be seen as a cause of bloat and the reduction of methane cannot be seen as a treatment of bloat. Therapeutic treatment against bloat is aimed at prevention of the formation of the foam layer in the rumen or its removal, not the prevention of production of ruminal gases. Moreover, carbon dioxide is the major gas produced during rumen fermentation. The present method is therefore neither intended nor suitable for treating bloat or for alleviating the symptoms thereof.

Thus, the present method of treatment is a non-therapeutic method of treatment, i.e. the method does not improve the health of an animal suffering from a particular condition, it does not prevent a particular disease or condition, nor does it to any extent affect the health of the ruminant in any other way, i.e. as compared to a ruminant not receiving the present method of treatment. The advantages of the present method are limited to environmental and/or economical aspects as explained before.

Taxonomically, a ruminant is a mammal of the order Artiodactyla that digests plant-based food by initially softening it within the animal's first stomach, known as the rumen, then regurgitating the semi-digested mass, now known as cud, and chewing it again. The process of rechewing the cud to further break down plant matter and stimulate digestion is called "ruminating". Ruminating mammals include cattle, goats, sheep, giraffes, bison, yaks, water buffalo, deer, camels, alpacas, llamas, wildebeest, antelope, pronghorn, and nilgai. The present invention is primarily concerned with methods of treating domesticated ruminants, especially those held for commercial livestock breeding. Thus, in a preferred embodiment of the invention, the ruminant is selected from the group of cattle, goats, sheep and buffaloes.

A preferred embodiment of the invention provides a method as defined above, wherein the combination of nitrate compound and sulphate compound is administered to the ruminant in an amount providing total dosage of nitrate and sulphate in excess of 0.05 g/kg body weight pet day. In a preferred embodiment said total dosage of nitrate and sulphate in the present method is within the range of 0.05-10 g/kg body weight per day, more preferably 0.1-5 g/kg body weight per day, most preferably 0.2-2.5 g/kg body weight per day.

In another preferred embodiment a method as defined herein before is provided, wherein the dosage of sulphate is within the range of 0.025-1.8 g/kg body weight per day, more preferably within the range of 0.05-0.9 g/kg body weight per day, most preferably 0.1-0.45 g/kg body weight per day.

In another preferred embodiment a method as defined herein before is provided, wherein the dosage of nitrate is within the range of 0.025-8 g/kg body weight per day, more preferably 0.05-4 g/kg body weight per day, most preferably 0.1-2 g/kg body weight per day.

The dosages defined herein as the amount per kg body weight per day concern the average amount of the respective compound during a given period of treatment, e.g. during a week or a month of treatment. The compounds may thus be administered every day, every other day, every other two days, etc., without departing from the scope of the invention. Preferably though, the method comprises daily administration of the combination of the nitrate compound and sulphate compound in the prescribed dosages. Even more preferably the combination is administered during feeding of the animal each time the animal is fed, in amounts yielding the above daily dosages.

As explained before, the capacity of rumen microflora to reduce nitrate to nitrite from animals not previously adapted to nitrate in their diet exceeds their capacity to reduce nitrite to ammonia. This may result in a net accumulation of nitrite in the rumen, which is readily absorbed across the rumen wall and converts the blood hemoglobin from the ferrous to the ferric form, methemoglobin, rendering the hemoglobin molecule incapable of transporting oxygen to the tissues. The resulting condition, methemoglobinemia, is a state of general anoxia, which in mild cases may depress animal performance, but in severe cases may result in death of the animal. The present inventors have established that, in the present method, careful, stepwise introduction of nitrate in the diet of sheep allows the rumen microflora to adapt and increase their capacity to reduce both nitrate and nitrite. Sheep slowly adapted to high nitrate diets, have been shown to experience no clinical signs of methemoglobinemia. Hence in a preferred embodiment of the invention, the method comprises a first phase of nitrate adaptation and a second phase of continued treatment, said first phase comprising two or more, preferably three or more, consecutive periods of at least 3 days, preferably at least 4 days, most preferably at least 5 days, wherein the average daily dosage of nitrate during each period is less than 100% of the average daily dosage administered during the second phase and wherein the average daily dosage during each period is higher than the average daily dosage during the period preceding it. In a preferred embodiment the increase in average daily dosage of nitrate from one period to the following is less than 1 g/kg body weight per day, preferably less than 0.5, more preferably less than 0.25, most preferably less than 0.1 g/kg body weight per day. Preferably, said second phase comprises a period of more than 5, 10, 25, 50, 100, 250 or 350 days of administering the combination of the nitrate compound and the sulphate compound in an average daily dosage within the range of 0.15-3 g/kg body weight.

The afore-defined methods, with or without initial adaptation phase, in a preferred embodiment, also comprise administering to the ruminant the nitrite reducing probiotic microorganism as defined herein before. It is particularly preferred to administer said probiotic microorganism in an amount of $1.0*10^5$-$1.0*10^{14}$ cfu/kg body weight per day, more preferably $1.0*10^7$-$1.0*10^{13}$ cfu/kg body weight per day, most preferably $1.0*10^9$-$1.0*10^{12}$ cfu/kg body weight per day. In a preferred embodiment, said methods comprise administration of probiotic microorganism and administration of lactic acid or lactate. It is particularly preferred to administer lactic acid or lactate in an amount of at least 0.025 g/kg body weight per day, more preferably 0.05-5 g/kg body weight per day, most preferably 0.1-2.5 g/kg body weight per day.

The present method may comprise, administration of the combination of the nitrate compound, the sulphate compound and, optionally, the nitrite reducing probiotic microorganism in accordance with the above described dosage regimens for a period of at least 5, 10, 25, 50, 100, 250 or 350 days. As noted herein before, an interesting aspect of the invention resides in the fact that the present method provides very persistent effectiveness in reducing enteric methanogenesis, i.e. the effect does not diminish over extended periods of treatment, e.g. as a result of increasing resistance of rumen or gut microorganisms, thereby rendering long-term treatment of the ruminant particularly feasible.

As will be clear from the above, the present method comprises oral administration of the combination of the nitrate compound and the sulphate compound and, optionally, the nitrite reducing probiotic microorganism. Preferably the treatment comprises oral administration of the compounded animal feed compositions and/or the animal feed supplement products as defined herein before, even though other liquid, solid or semi-solid orally ingestible compositions may be used without departing from the scope of the invention, as will be understood by those skilled in the art.

In accordance with the foregoing, still a further aspect of the invention concerns the use of a composition comprising a combination of the nitrate compound and the sulphate compound for non-therapeutic reduction of gastro-intestinal methane production in a ruminant. It is preferred that the use comprises administering the combination of the nitrate compound and the sulphate compound to the ruminant in an amount providing a total dosage of nitrate and sulphate exceeding 0.05 g/kg body weight per day. Preferably the nitrate compound and sulphate compound are used in the dosages as described herein before. In another preferred embodiment the use additionally comprises administering to the ruminant the nitrite reducing probiotic microorganism in the dosages as described herein before. Still more preferably, the use of any one of the compositions as defined herein before is provided for non-therapeutic reduction of gastro-intestinal methane production in a ruminant Another aspect of the invention concerns therapeutic treatments of nitrate-supplemented ruminants. As explained before, it is known that nitrate supplementation of ruminants will aid in lowering gastro-intestinal methanogenesis but also increases the risk or incidence of nitrite accumulation, the so-called 'nitrate toxicity syndrome' and/or methemoglobinemia, reducing the blood's capacity to transport oxygen to the animals' tissues. In addition, nitrite accumulation in the rumen is known to reduce microbial activity in the rumen, which inter alia may reduce feed intake by the animal. As explained before, the present inventors have established that administration to such nitrate supplemented ruminants of a sulphate compound, preferably in combination with a nitrite reducing probiotic microorganism, greatly reduces or even prevents these adverse effects.

Hence, an aspect of the invention concerns a method of treating or preventing nitrite accumulation, 'nitrate toxicity syndrome' and/or methemoglobinemia in nitrate supplemented ruminants comprising administering to said ruminant an effective amount of the sulphate compound, optionally in combination with an effective amount of the nitrite reducing probiotic microorganism.

Another aspect of the invention concerns a preparation comprising the sulphate compound, optionally in combination with the nitrite reducing probiotic microorganism, for use in the method of treating or preventing nitrite accumulation, 'nitrate toxicity syndrome' and/or methemoglobinemia in nitrate supplemented ruminants.

Still another aspect of the invention concerns the use of the sulphate compound, optionally in combination with the nitrite reducing probiotic microorganism, in the manufacture of the preparation for use in a method of treating or preventing nitrite accumulation, 'nitrate toxicity syndrome' and/or methemoglobinemia in nitrate supplemented ruminants.

In accordance with the foregoing, the method of treating and/or preventing nitrite accumulation, 'nitrate toxicity syndrome' and/or methemoglobinemia typically comprises administering said compositions in amounts sufficient to provide a total dosage of sulphate within the range of 0.025-1.8 g/kg body weight per day, more preferably 0.05-0.9 g/kg body weight per day, most preferably 0.1-0.45 g/kg body weight per day, and, optionally, a total dosage of said probiotic microorganism of of $1.0*10^5$-$1.0*10^{14}$ cfu/kg body weight per day, more preferably $1.0*10^7$-$1.0*10^{13}$ cfu/kg body weight per day, most preferably $1.0*10^9$-$1.0*10^{12}$ cfu/kg body weight per day. In a preferred embodiment, said method comprises administration of probiotic microorganism and administration of lactic acid or lactate. It is particularly preferred to administer lactic acid or lactate in an amount of at least 0.025 g/kg body weight per day, more preferably 0.05-5 g/kg body weight per day, most preferably 0.1-2.5 g/kg body weight per day As used herein, the term 'nitrate supplemented ruminant' refers to a ruminant receiving substantial amounts of nitrate, typically through the feed. Preferably the ruminant is supplemented nitrate in amounts sufficient for lowering gastro-intestinal methanogenesis, more preferably in amounts in excess of 0.025 g/kg body weight per day, most preferably 0.05-8 g/kg body weight per day. As will be understood by those skilled in the art, the method may be equally suitable to treat or prevent nitrite accumulation, 'nitrate toxicity syndrome' and/or methemoglobinemia in ruminants receiving substantial amounts of nitrate for other purposes or even unintentionally, e.g. as a result of environmental conditions.

The invention as defined here above will be illustrated and explained in more detail in the following experimental part, which is not intended to limit the scope of the invention in any way.

EXAMPLE I

Nitrate and Sulphate in Methane Mitigation

Material and Methods

Animals and Housing

In the current experiment the methane reducing properties of dietary nitrate and sulphate were evaluated. Both nitrate and sulphate were slowly introduced in the diet during a 4-week adaptation period. Feed intake and growth were monitored during the experiment. It was hypothesied that both dietary nitrate and sulphate would reduce methane emissions from enteric fermentation.

The Animal Care and Use Committee of the Animal Sciences Group, WUR, Lelystad approved the experimental protocol of this experiment. The experiment was conducted with 20 male Texel Cross lambs, weighing 42.9±4.3 kg (mean±standard deviation) at the start of the experiment. During a four-week adaptation phase to the dietary additives, animals were housed in individual calf hutches to allow individual feeding. Sheep were weighed weekly to monitor growth during the entire experiment.

After the adaptation period four animals (one block) were housed in indirect respiration calorimetry chambers for a week to determine gaseous exchange. In the following weeks a new block of sheep was introduced to the chambers each week. Each respiration chamber housed an individual sheep. The respiration calorimetry chambers used are described in detail in Verstegen et al. (1987). Temperature was maintained at 15° C., and relative humidity was set at 70%. Ventilation rate was 70 l/min for one type of chambers and 90 l/min for the other type.

Air going into and out of the chambers was analyzed for $CO_2$, $O_2$ and $CH_4$ in 9-min intervals. Net production or consumption of these gases was calculated from the difference in concentrations between in and outgoing air multiplied by air flow and subsequently recalculated to standard circumstances (0° C., 101 kPa, no water vapour).

Experimental Design

The experiment was designed as a 2×2 factorial design, with nitrate and sulphate as factors. Animals were blocked by weight and subsequently within a block randomly allotted to one of four dietary treatments: CON, $NO_3$, $SO_4$ or $NO_3+SO_4$.

Feeding

The basal diet consisted of 74% maize silage, 16% chopped barley straw, 9% formaldehyde treated soybean meal and 1% of a mineral premix on a DM-basis. The dietary additives were included in a mixture (table 1) that was added to the basal diet at 10% of diet DM. At feeding, the premixes were hand-mixed into the diets. Water was freely available during the experiment. Nitrate was supplemented from a commercially available source (Calcinit, Yara) and supplemental $SO_4$ was added to the diet in the form of anhydrous $MgSO_4$.

During the adaptation phase, sheep were introduced to the experimental premixes in steps of 25% per week. Lambs were fed once daily at 8:30. Before morning feeding, orts were removed from the feed bins and weighed to determine voluntary feed intake. During the week in the respiration chambers, feed availability was restricted to 95% of the feed consumed by the animal consuming the least feed within a block in the week prior to housing in the respiration chambers. Feed restriction was applied to avoid interactions between the effect of the additives on DMI and the effect on methane production.

Nitrate in the experimental diets was exchanged for urea on the control diet to maintain isonitrogenous diets. Limestone was added to the control diet to ensure equal Ca-intake between treatments. MgO was included in the diet to obtain similar Mg-levels between diets. The volume of the different additions to the diets was different for each treatment, and wood cellulose was used to balance for this.

TABLE 1

Composition of the mixtures containing the experimental additives (% of DM)

| | CON | $NO_3$ | $SO_4$ | $NO_3 + SO_4$ |
|---|---|---|---|---|
| Formaldehyde treated soybean meal | 22 | 22 | 22 | 22 |
| Urea | 15 | | 15 | |
| Nitrate source[2] | | 38 | | 38 |
| MgSO4 (anhydrous) | | | 33 | 33 |
| MgO | 13 | 13 | | |
| CaCO3 | 22 | | 22 | |
| Wood cellulose | 28 | 27 | 8 | 7 |
| Added nitrate in diet | 0 | 2.9 | 0 | 2.9 |
| Added sulphate in diet | 0 | 0 | 0.7 | 0.7 |

[2]chemical formula $5Ca(NO_3)_2 \cdot NH_4NO_3 \cdot 10H_2O$

Blood, Rumen and Liver Sampling

Blood was sampled at d2, d8, d15, d22 and d28 at 1, 3 and 5 h post-feeding. Days 2, 8, 15 and 22 all were 1 day after an incremental step of 25% of the experimental premix in the diet. On day 28, lambs had been on 100% of the dietary treatments for one week. Blood samples were taken in heparin containing collection tubes (Vacutainers) and stored in the refrigerator directly after sampling. At the end of the sampling day, samples were dispatched for analyses and were analyzed the next day. The methemoglobin content of the blood was determined by the methods described in Evelyn and Malloy (1938).

After completion of the period in the respiration chambers, sheep were slaughtered and rumen fluid samples (200 ml) were taken from the rumen as soon as possible after slaughter. Samples were immersed in ice water directly after sampling to stop microbial fermentation and frozen once all the samples were taken. At slaughter, duplicate samples of liver were taken, chilled and frozen for later assessment of vitamin A status.

Results and Discussion

Methemoglobin Contents of Blood During Adaptation Period

During supplementation of the diet with 25% or 50% of the final premix inclusion rate none of the sheep had a positive blood MetHb-content (<2% of Hb). When 75% of the inclusion rate was included in the diet one sheep on the $NO_3$-diet tested positive at 3 h post feeding, but the value was only 3% of Hb. When sheep were on the 100% inclusion rate for one week (d28) two sheep on the $NO_3$-treatment tested positive with MetHb-values of 7% and 3% of Hb respectively at 3 h post-feeding. The sheep on the control diet and both sulphate containing diets never had MetHb-levels higher than 2% of Hb (detection limit), possibly indicating that S plays a role in the reduction of nitrite in the rumen.

The adaptation period of 4 wk apparently was sufficient to prevent any significant problems associated with nitrite toxicity and methemoglobinemia. A similar finding was reported by Alaboudi and Jones (1985). Nitrate levels of 2.9% of DM would be considered lethal for unadapted ruminants, but adaptation apparently enabled the rumen bacteria to increase their nitrite reducing capacity.

Feed Intake and Growth During the Adaptation to Dietary Nitrate and Sulphate

Feed intake was not different as a result of the addition of $NO_3$ or $SO_4$ (table 2), but tended to be lower when the full dose of nitrate was provided. However, with inclusions more than 25% of the final inclusion rate, feed intake was consistently reduced (approximately 9% in the period beyond week 1) as a result of the inclusion of $NO_3$. The low number of animals used in this study hinders drawing conclusions on the effects on feed intake, but the consistent lower feed intake should not be ignored. Bruning-Fann and Kaneene (1993) report that in sheep negative effects on feed intake have been observed when the dietary nitrate levels exceeded 3% of diet DM. This reduction in feed intake may be related to a nitrite-induced depression of cell wall digestion as was demonstrated in vitro by Marais et al. (1988).

Feeding $NO_3$ or $SO_4$ did not affect body weight gain (table 3).

TABLE 2

Feed intake (g/lamb/day) during the 4-week adaptation stage to the dietary additives

| | Main Effects | | | | | | | | Interaction | |
|---|---|---|---|---|---|---|---|---|---|---|
| | Nitrate | | | | Sulphate | | | | Nitrate * Sulphate | |
| | No | Yes | P-value | s.e.m. | No | Yes | P-value | s.e.m. | P-value | s.e.m. |
| Week 1 | 2682 | 2686 | 0.995 | 85.7 | 2644 | 2724 | 0.500 | 84.2 | 0.112 | 118.6 |
| Week 2 | 2836 | 2591 | 0.105 | 100.7 | 2657 | 2770 | 0.425 | 98.9 | 0.156 | 139.3 |
| Week 3 | 2741 | 2526 | 0.177 | 103.8 | 2650 | 2618 | 0.836 | 102.0 | 0.39 | 143.7 |
| Week 4 | 2696 | 2411 | 0.096 | 104.2 | 2650 | 2457 | 0.216 | 102.3 | 0.136 | 144.1 |

TABLE 3

Body weight (BW; kg/lamb) and body weight gain (BWG; kg/lamb/week) during the adaptation stage to the dietary additives

| | Main Effects | | | | | | | | Interaction | |
|---|---|---|---|---|---|---|---|---|---|---|
| | Nitrate | | | | Sulphate | | | | Nitrate * Sulphate | |
| | No | Yes | P-value | s.e.m. | No | Yes | P-value | s.e.m. | P-value | s.e.m. |
| BW day 0 | 42.7 | 43.0 | 0.605 | 0.51 | 43.2 | 42.4 | 0.285 | 0.51 | 0.433 | 0.72 |
| BW day 7 | 43.8 | 43.6 | 0.810 | 0.55 | 44.2 | 43.1 | 0.199 | 0.55 | 0.137 | 0.77 |
| BW day 14 | 44.9 | 44.7 | 0.741 | 0.57 | 45.2 | 44.3 | 0.287 | 0.57 | 0.176 | 0.80 |
| BW day 21 | 45.2 | 45.2 | 0.985 | 0.72 | 45.7 | 44.7 | 0.336 | 0.72 | 0.240 | 1.08 |
| BW day 28 | 45.7 | 45.5 | 0.858 | 0.81 | 46.4 | 44.8 | 0.182 | 0.81 | 0.346 | 1.15 |
| BWG week 1 | 1.11 | 0.54 | 0.363 | 0.426 | 0.95 | 0.70 | 0.685 | 0.426 | 0.685 | 0.602 |
| BWG week 2 | 1.16 | 1.08 | 0.815 | 0.236 | 1.04 | 1.20 | 0.641 | 0.236 | 0.815 | 0.334 |
| BWG week 3 | 0.30 | 0.59 | 0.482 | 0.282 | 0.51 | 0.38 | 0.750 | 0.399 | 0.788 | 0.399 |
| BWG week 4 | 0.48 | 0.25 | 0.715 | 0.436 | 0.67 | 0.06 | 0.342 | 0.436 | 0.836 | 0.616 |
| BWG overall | 3.05 | 2.46 | 0.508 | 0.611 | 3.17 | 2.34 | 0.356 | 0.611 | 0.356 | 0.864 |

TABLE 4

Feed intake, gaseous exchange and heat production during the measuring week in the respiration chambers

| | Main Effects | | | | | | | | Interaction | |
|---|---|---|---|---|---|---|---|---|---|---|
| | Nitrate | | | | Sulphate | | | | Nitrate * Sulphate | |
| | No | Yes | P-value | s.e.m. | No | Yes | P-value | s.e.m. | P-value | s.e.m. |
| Feed intake (g/lamb/day) | 2.39 | 2.38 | 0.782 | 0.02 | 2.39 | 2.38 | 0.631 | 0.020 | 0.350 | 0.03 |
| Methane production (l/lamb/day) | 23.5 | 15.4 | <0.001 | 1.06 | 21.5 | 17.5 | 0.02 | 1.06 | 0.94 | 1.50 |
| Methane production (l/kg$^{0.75}$/day) | 1.4 | 0.9 | <0.001 | 0.07 | 1.3 | 1.0 | 0.05 | 0.07 | 0.90 | 0.10 |
| Methane production (l/kg feed intake/day) | 9.85 | 6.53 | <0.001 | 0.44 | 8.99 | 7.4 | 0.025 | 0.44 | 0.91 | 0.62 |
| $CO_2$-production (l/kg$^{0.75}$/day) | 26.1 | 24.9 | 0.03 | 0.345 | 25.0 | 26.1 | 0.043 | 0.345 | 0.487 | 0.49 |
| $O_2$-consumption (l/kg$^{0.75}$/day) | 26.6 | 25.0 | 0.006 | 0.339 | 25.2 | 26.3 | 0.038 | 0.339 | 0.552 | 0.48 |
| Heat production (kJ/kg$^{0.75}$/day) | 558 | 527 | 0.008 | 6.9 | 531 | 555 | 0.03 | 6.9 | 0.517 | 9.75 |

Effects of $NO_3$ and $SO_4$ on Gaseous Exchange

The fluxes of gases determined in the respiration chambers are shown in table 4. The limit-feeding that was applied during this part of the experiment resulted in very similar feed intake between treatments. Methane production was lowered by 34% as a result of the addition of the nitrate source to the diet.

The sheep on the $NO_3$-treatment in our experiment consumed on average 24.9 g $NO_3$ per day, which would theoretically lower methane production by 6.4 g. The actual decrease in methane production on the NO3-treatment was 8.1 l, which corresponds to 5.8 g of CH4 ($CH_4$=0.714 g/l). Thus, the decrease in methane production is actually somewhat lower than can be explained by stoichiometry, which may be explained by incomplete reduction of nitrate to ammonia or use of nitrate in other processes than dissimilatory nitrate reduction. The nitrate source used in this study was highly soluble and it is therefore likely that most of the nitrate was available for reduction in the rumen. However, most of the dissolved nitrate would have been in the liquid phase of the rumen and may have passed out of the rumen before being reduced.

The addition of sulphate led to a reduction of 19% in daily methane production.

In our study, sheep on the $SO_4$-treatment consumed on average 27.0 g $SO_4$/day, which would correspond to a methane reduction of 4.5 g. The actual observed decrease in methane reduction was 4 l, or 2.9 g. The difference in the theoretical capacity for $SO_4$ as a hydrogen sink and its observed capacity to reduce methane emission may be in the solubility of MgSO4 in the rumen.

Sheep on the $SO_4$-treatments were fed a considerable amount of S in the diet (7.4 g added S/kg DM). This level is well above the maximum recommendations as indicated by NRC (4 g/kg DM). Feeding above this upper limit increases the risk of polioencephalomalacia, due to high levels of $H_2S$ occurring in the rumen headspace and the subsequent inhalation of $H_2S$. Results from this experiment do, however, show that $SO_4$ is effective in reducing methane production. When fed within recommended levels (2-4 g S/kg DM), it is expected that SO4 will still have a reducing effect on methane production.

Oxygen consumption and $CO_2$-production were both lower as a consequence of the nitrate treatment. High doses of nitrate in ruminant diets have been reported to cause methemoglobinemia, reducing the blood's capacity to transport oxygen to the animals' tissues. However, in this experiment blood was sampled on a regular basis and slightly elevated MetHb-levels were only found in two sheep (maximum level was 7% of Hb) and appears unlikely to explain the lower $O_2$-consumption. The lower $O_2$-consumption may reflect a different metabolism when nitrate is fed. Sar et al. (2004) also observed a lower $O_2$-consumption and lower $CO_2$-production when 0.9 g $NO_3$/$kg^{0.75}$ of BW was intraruminally dosed to sheep. In this study considerably more nitrate was fed (1.4 g $NO_3$/$kg^{0.75}$ of BW), but MetHb-levels in our study were considerably lower (18.4% of Hb in the study of Sar et al.). This is probably due to the absence of an adaptation period in the study of Sar et al. (2004) and the fact that nitrate was dosed as a solution into the rumen. In another study (Takahashi et al., 1998) dosed $NaNO_3$ into the rumen of sheep at a rate of 1.5 g/kg $BW^{0.75}$, which was very similar to the concentration used in our study. Concentrations of MetHb of over 30% were observed and from the study data it was concluded that for each 10% increase in MetHb, oxygen consumption decreases by 10.3%. In our study a reduction in oxygen consumption of 6% was observed. Using the regression equation by (Takahashi et al., 1998) this would mean that the animals would have had MetHb-levels of approximately 5%. In two animals similar levels (3 and 7% of Hb) were actually observed.

Methane production on the control treatment was typical for sheep limit-fed once daily. Animals were fed at 8 AM, after which methane production progressively increased to reach maximum methane production at 5-6 h after feeding. Since animals were limit-fed and only fed once daily, methane production successively declined after the peak. The addition of nitrate to the ration invoked a markedly different methane production pattern; immediately after feeding methane production rate remained at a far lower level and it was hypothesized that in this period hydrogen was utilized for nitrate reduction, thereby limiting $H_2$-availability for methanogenesis. Ten hours after feeding, methane production rate was not different from the control treatment any longer, probably reflecting the absence of nitrate containing feed and a return to methanogenesis as H-sink. Although methane production was significantly lower after feeding as a result of the nitrate fed, methane production was never reduced to 0 and nitrate reduction and methanogenesis occurred simultaneously. The basal level of methane production may at least be partly explained by methane production from hindgut fermentation. It is unlikely that nitrate reaches the hindgut without being reduced and nitrate feeding would therefore probably not influence methane production in this part of the gastrointestinal tract.

Methane production rate from the $SO_4$-treatment was never different from the control treatment but was consistently lower than the control treatment over the entire 24 h-period. The same was observed when the $SO_4$-treatment was compared to the $NO_3$+$SO_4$-treatment. Clearly, the effects of $NO_3$ and $SO_4$ on methane production are complimentary and the effect of $SO_4$ seems to be less dependent of the availability of feed containing $SO_4$.

Results of the experiment are also depicted in the graph of FIG. 1, showing the methane production (1/hr) over the course of a 24 period in the groups receiving either the basal diet or one of the three experimental diets.

Oxygen Consumption Over the Course of a 24-h Period

Directly after feeding at 8 AM oxygen consumption was 10-18% lower for the $NO_3$-treatment. The difference in oxygen consumption between treatments disappeared after 16 PM. This phenomenon coincides with the markedly reduced methane production in the period after feeding for the $NO_3$-treatment. It is hypothesized that in this period significant nitrate reduction occurred in the rumen, with production of nitrite as an intermediate on the $NO_3$-treatment. The presence of nitrite during this period might explain the lower oxygen consumption of the $NO_3$-treatment. Although MetHb-levels beyond 7% of Hb were never observed for the $NO_3$-treatment, a definite reduction in oxygen consumption was observed. Storage time of the samples (samples were analyzed approximately 24 h after sampling) might explain the lower than expected MetHb-levels found.

On the $NO_3$+$SO_4$ treatment, oxygen consumption was only lower directly after feeding (9 AM) and recovered to the same level as the control treatment after this time point. The addition of SO4 apparently alleviates the depression in oxygen consumption invoked by the feeding of nitrate. Possibly, $SO_4$ was reduced to $H_2S$ in the period directly after feeding and played a role in the acceleration of reduction of nitrite as was proposed by. A clear dose-dependent acceleration of nitrite reduction was found earlier when sulphide was added to rumen fluid in vitro (Takahashi et al., 1989). The acceleration in nitrite reduction was much less when $SO_4$ was added to the medium and therefore it appears plausible that it was $H_2S$, which actively restored oxygen consumption in our experiment.

Figure 2:
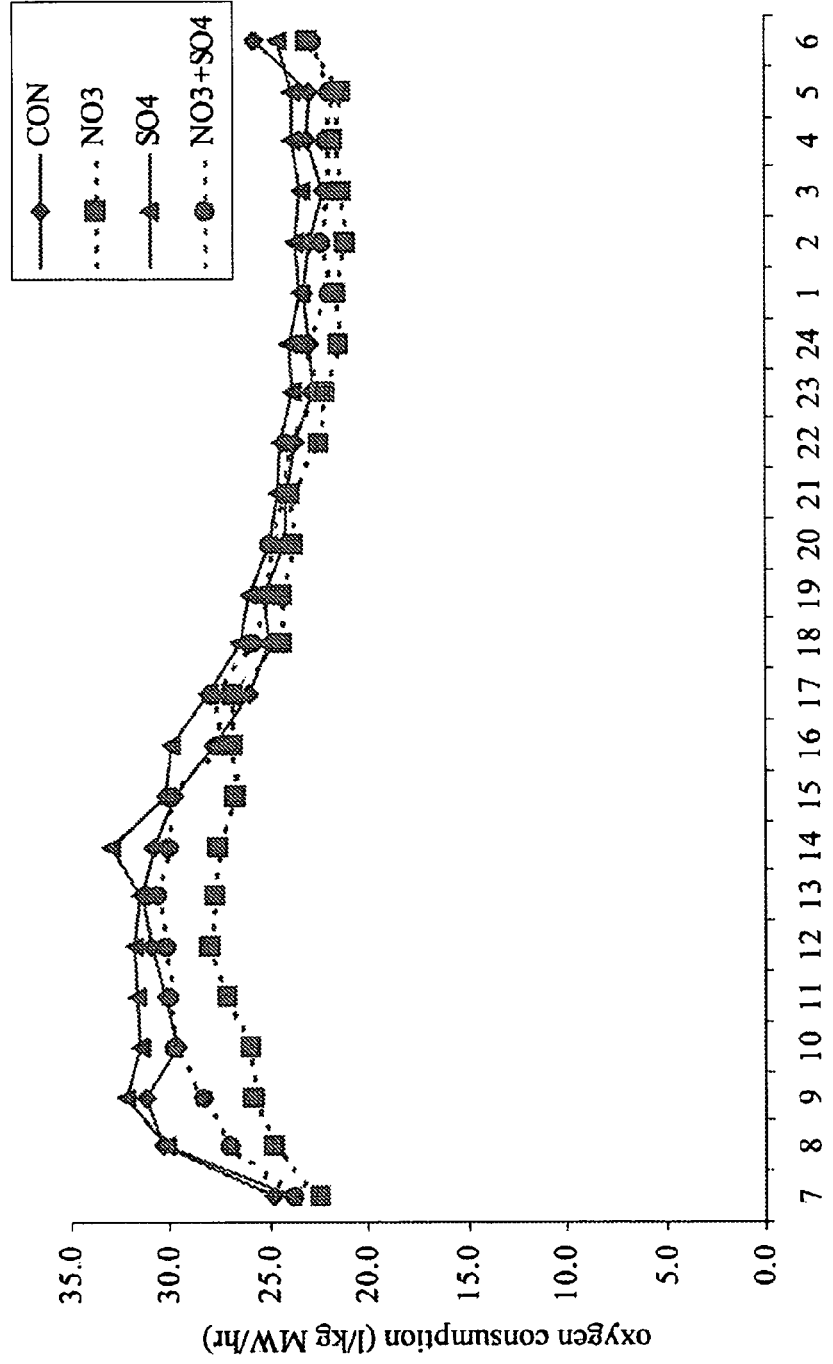
FIG. 2 is a graph showing the oxygen consumption (1/kg MW/hr) over the course of a 24 period in male Texel cross lambs receiving a basal diet or one of three experimental diets, which were supplemented with a nitrate compound, a sulphate compound or a combination of a nitrate compound and a sulphate compound.

Results of the experiment are also depicted in the graph of FIG. 2, showing the oxygen consumption (1/kg MW/hr) over the course of a 24 period in the groups receiving the basal diet or one of the three experimental diets.

EXAMPLE II

Effect of Sulphate on Methemoglobinemia in Nitrate Supplemented Cattle

The effect of dietary sulphate intake on the concentration of methaemoglobin in blood of cows supplemented with nitrate was evaluated. It was hypothesized that dietary sulphate would reduce the accumulation of nitrite in the rumen of cows fed nitrate and consequently prevent the formation of methaemoglobin in blood.

Material and Methods

Experimental Design

The experiment was a randomized block design, with 4 animals per block and different sulphate doses as treatments. Animals were blocked by milk yield and subsequently within a block randomly allotted to one of four dietary treatments: $NO_3$, $NO_3$+low $SO_4$, $NO_3$+medium $SO_4$, $NO_3$+high $SO_4$.

Feeding

The basal diet consisted of 45% maize silage, 7.5% dry alfalfa, 4.1% chopped barley straw, and 42% of a concentrate premix on a DM-basis. The dietary additives were included in the premix (table 5). At feeding, the premixes were delivered to cows as part of a Total Mixed Ration. Water was freely available during the experiment. Nitrate was supplemented from a commercially available source (Calcinit, Yara AS, Norway) and supplemental $SO_4$ was added to the diet in the form of anhydrous $MgSO_4$.

TABLE 5

Composition of the mixtures containing the experimental additives (% of DM)

| | | % DM-basis | | |
| --- | --- | --- | --- | --- |
| Treatment | Description | NO3 | Added product | SO4 | Added product |
| A | $NO_3$ | 3 | 3.96 | 0.15 | 0.00 |
| B | $NO_3$ + low $SO_4$ | 3 | 3.96 | 0.23 | 0.32 |
| C | $NO_3$ + medium $SO_4$ | 3 | 3.96 | 0.32 | 0.63 |
| D | $NO_3$ + high $SO_4$ | 3 | 3.96 | 0.40 | 0.95 |

During the adaptation phase, cows were introduced to the experimental premixes in steps of 25% per week. (Table 6).

TABLE 6

Composition of the experimental concentrate combinations during the adaptation phase

| | % | |
| --- | --- | --- |
| Feed | Concentrate control | Concentrate premix A, B, C or D |
| Day 8-14 | 75 | 25 |
| Day 15-21 | 50 | 50 |
| Day 22-28 | 25 | 75 |
| Day 29-35 | 0 | 100 |

Blood Sampling

Blood was sampled 3 h post-feeding twice a week throughout the experiment to closely monitor the concentration of methaemoglobin. Blood was collected into evacuated tubes containing heparin, plunged immediately into ice-cold water and stored in a refrigerator at 4 C. At the end of each sampling day, samples were dispatched for analysis and were analyzed the next day. The methaemoglobin content of the blood was determined by the method of Evelyn and Malloy (1938). On day 37, when nitrate was fed at its maximum inclusion rate (3% of nitrate on DM-basis), blood sampling was performed more frequently (−0.5 h, 0.5 h, 1.5 h, 3 h, 5 h and 8 h post-feeding) in order to establish the kinetics of nitrate and its various metabolites in the plasma.

Results and Discussion

Methemoglobin Contents of Blood During Adaptation Period

None of the cows had detectable blood methaemoglobin during the supplementation of the diet with 25% or 50% of the final nitrate inclusion rate. When nitrate was added to the diet at 75% of the final inclusion rate, cows that were not supplemented with sulphate exhibited elevated blood haemoglobin at 3 h post feeding. By contrast, cows given sulphate in their diet tested negative for methaemoglobin, irrespective of the amount of S supplied. At the 100% inclusion rate of nitrate, all treatments exhibited a rise in blood methaemoglobin, although the rise was more pronounced for cows on nitrate alone, compared with those given nitrate and sulphate. Among cows supplemented with sulphate, it wasn't possible to distinguish an effect of the dose of sulphate (see table 7). It was concluded that sulphate was able to counteract the accumulation of nitrite in the rumen, hence preventing (at moderate nitrate addition) or reducing (at high nitrate addition) the formation of methaemoglobin in the blood.

TABLE 7

Blood methaemoglobin (% of haemoglobin)

| | $NO_3$ | $NO_3$ + low $SO_4$ | $NO_3$ + medium $SO_4$ | $NO_3$ + high $SO_4$ | P-value |
| --- | --- | --- | --- | --- | --- |
| Blood methaemoglobin (% of haemoglobin) | 13.1$^a$ | 2.6$^b$ | 6.0$^b$ | 4.8$^b$ | 0.063 |

Means with different superscripts are significantly different (P < 0.1)

Figure 3:
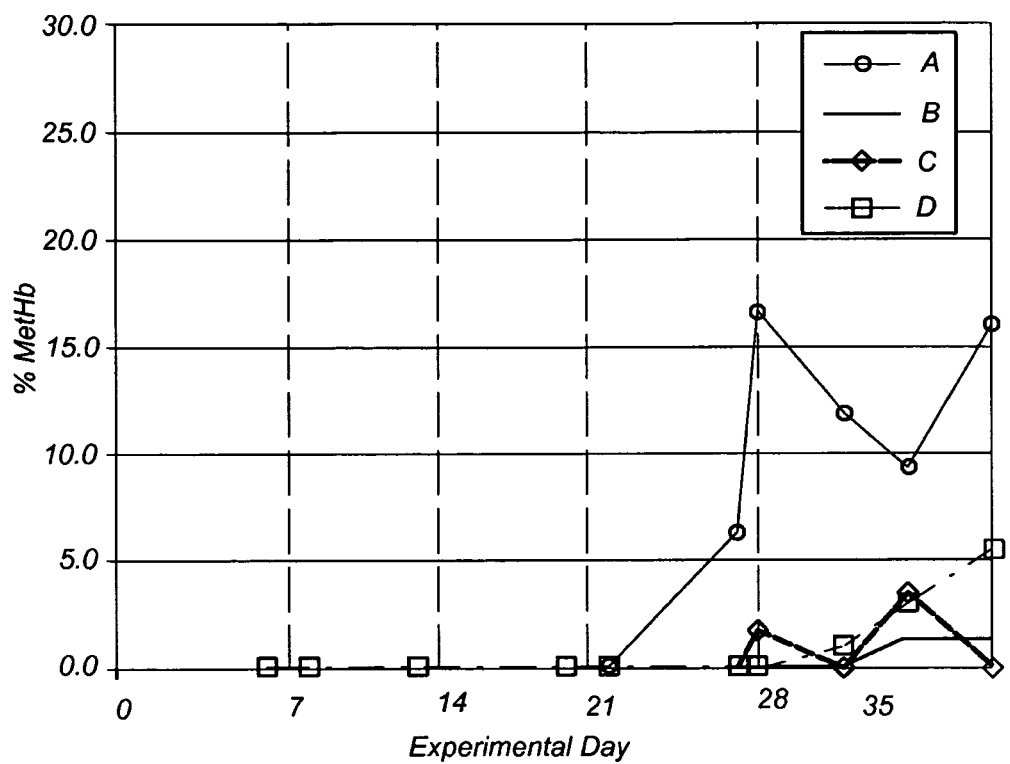
FIG. 3 is a graph showing the concentration of methaemoglobin in blood of cows receiving either one of four experimental diets, which were supplemented with nitrate, or one of three combinations of nitrate and increasing amounts of sulphate.

Results of the experiment are also depicted in the graph of FIG. 3, showing the concentration of methaemoglobin in blood cows receiving either one of the four experimental diets.

EXAMPLE III

Effect of *Megasphaera elsdenii* and *Selenomonas ruminantium* on the Rate of Nitrate and Nitrite Reduction in the Rumen Fermentation Model In the present experiment the kinetics of nitrate reduction in an in vitro rumen fermentation system were studied and the effects thereon by *M. elsdenii* and *S. ruminantium*.

Materials and Methods

Feed used in rumen simulation was 1 gram of dry matter and composed of grass silage (0.5 g dry matter) and commercial compound feed, 0.5 g dry matter. The treatments were as indicate in the following table:

| treatment | Amendments |
| --- | --- |
| 1. | No amendments |
| 2. | 57 mg of Calcinit/40 ml*$^)$ |
| 3. | 57 mg of Calcinit + 10 μl *M. elsdenii*/40 ml*$^)$ |
| 4. | 57 mg of Calcinit + 100 μl *M. elsdenii*/40 ml*$^)$ |
| 5. | 57 mg of Calcinit + 1000 μl *M. elsdenii*/40 ml*$^)$ |
| 6. | 57 mg of Calcinit + 10 μl *M. elsdenii* + 100 mg Na-lactate/40 ml*$^)$ |
| 7. | 57 mg of Calcinit + 100 μl *M. elsdenii* + 100 mg Na-lactate/40 ml*$^)$ |
| 8. | 57 mg of Calcinit + 1000 μl *M. elsdenii* + 100 mg Na-lactate/40 ml*$^)$ |
| 9. | 57 mg of Calcinit + 10 μl *M. elsdenii* + 200 mg Na-lactate/40 ml*$^)$ |
| 10. | 57 mg of Calcinit + 100 μl *M. elsdenii* + 200 mg Na-lactate/40 ml*$^)$ |
| 11. | 57 mg of Calcinit + 1000 μl *M. elsdenii* + 200 mg Na-lactate/40 ml*$^)$ |
| 12. | 57 mg of Calcinit + 100 mg Na-lactate/40 ml*$^)$ |
| 13. | 57 mg of Calcinit + 200 mg Na-lactate/40 ml*$^)$ |
| 14. | 57 mg of Calcinit + 10 μl *S. ruminantium*/40 ml*$^)$ |
| 15. | 57 mg of Calcinit + 100 μl *S. ruminantium*/40 ml*$^)$ |
| 16. | 57 mg of Calcinit + 1000 μl *S. ruminantium*/40 ml*$^)$ |

-continued

| treatment | Amendments |
|---|---|
| 17. | 57 mg of Calcinit/40 ml*) |
| 18. | No amendments |

*)Treatments 2 to 17 contain 7.52 mg MgSO₄/40 ml.

All the treatments were run in quadruplicates, the total number of simulation vessels being 72.

Dry feed components and Calcinit were weighed in serum bottles, the bottles flushed with $CO_2$ passed through a hot copper catalyst for $O_2$ scavenging, and, sealed with thick butyl rubber stoppers. 36.5 ml of anaerobic, reduced, temperature adjusted (+37° C.) buffer solution was introduced into each simulation vessel under the oxygen free $CO_2$ flow. Overnight grown bacterial cultures, $MgSO_4$ solution, lactate solution and the buffer solution to equalise the total liquid volume to 1.5 ml/vessel were added. Finally, 2 ml of fresh, strained rumen fluid was added in the serum bottles, the final volume being 40 ml. This inoculation started the actual rumen simulation. Inoculation time for each vessel was registered and taken into account when sampling and stopping the fermentation.

Rumen fermentation simulation was continued for 12 hours at 37° C. During the fermentation the total gas production was measured after 2, 4, 6, 9 and 12 hours of simulation to get an idea on the general metabolic activity of the rumen microbes.

All the gas produced during the 12 hours in each simulation vessel was individually collected from each of the 72 vessels into an evacuated 2 liter infusion bottles which, had pre-introduced ethane as an internal standard. These samples were analysed for methane to see the effect of treatments on the total methane produced by rumen bacteria during the 12 hours. The analysis was performed by gas chromatography using flame ionisation detector and pure methane and ethane as standards.

At 4 and 12 hours all the simulation vessels were analysed for volatile fatty acids (VFAs) and lactic acid (collectively referred to as SCFAs). The acids were analysed by gas chromatography using a packed column for the analysis of free acids. The SCFAs quantified were acetic, propionic, butyric, iso-butyric, 2-methyl-butyric, valeric, iso-valeric and lactic acids.

$NO_3$ and $NO_2$ were analysed from all simulation vessels at 0, 2, 4 and 12 hours. The method was spectrophotometric and based on nitrate reduction with vanadium(III) combined with detection by the acidic Griess reaction.

$NH_4$ was analysed from all simulation vessels at 0, 2, 4 and 12 hours. The method was colorimetric and based on phenol-hypochlorite reaction.

Statistical analysis consisted of two-tailed t-tests for all measured parameters. The tests were performed against the treatment with Calcinit and $MgSO_4$ amendment (treatments 2 and 17). t-test was chosen to let the individual treatments be independent of the other treatments tested simultaneously. The results are marked in the figures, wherein $0.01 \leq p\text{-value} < 0.05$ is indicated as: *; $0.001 \leq p\text{-value} < 0.01$ is indicated as: ; $0.0001 \leq p\text{-value} < 0.001$ is indicated as: *; and $p\text{-value} < 0.0001$ is indicated as: ****.

Results

Effect of Treatments on the Total Gas Production

Figure 4A:
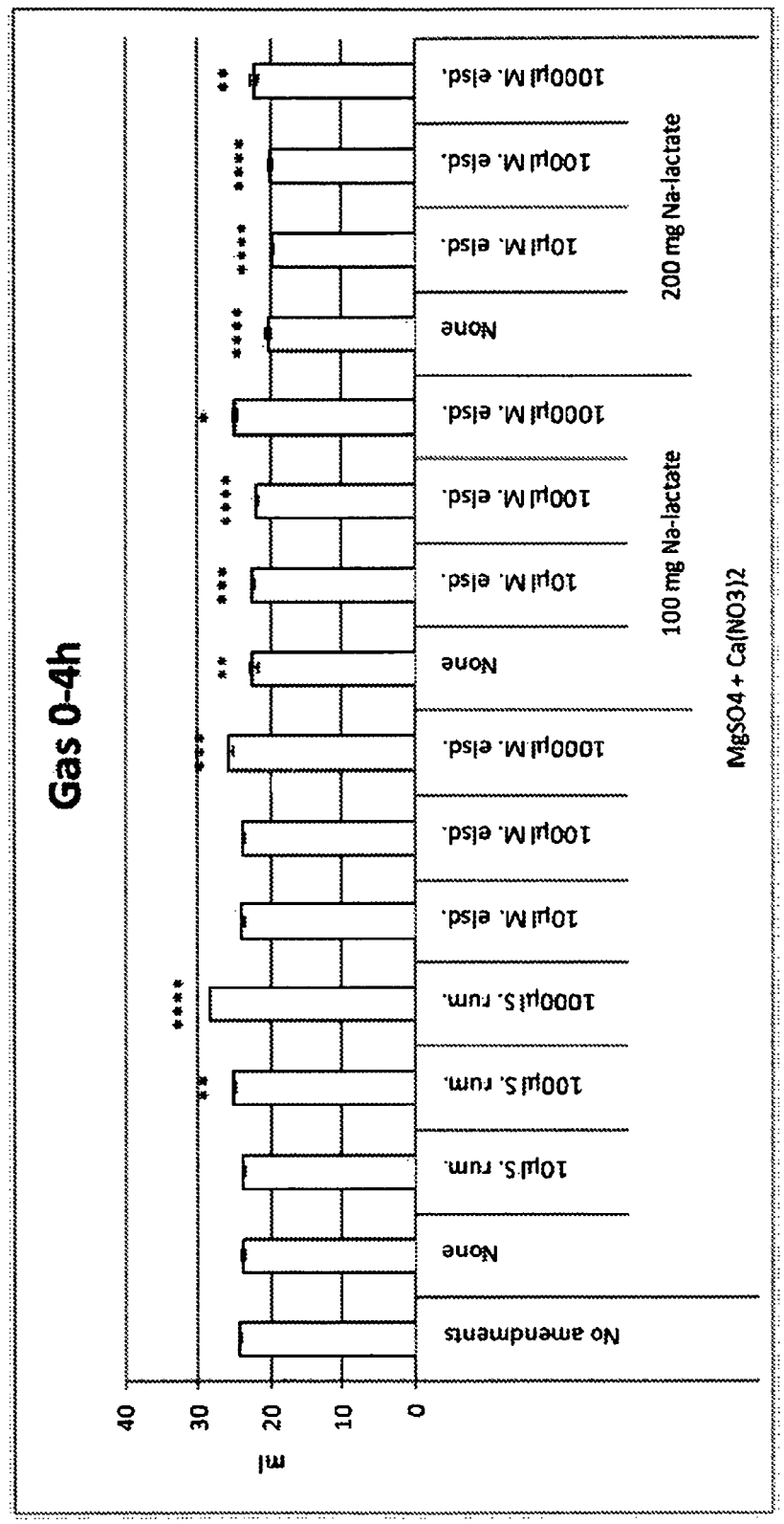
FIG. 4 shows the gas production in the rumen simulation with various test products. Panels A to C show the cumulative gas production at indicated time points. The error bars indicate SE between replicate simulation vessels and asterisks the statistical difference to the Ca(NO3)2+MgSO4 containing control (referred to as "None") with the t-test.
Figure 4B:
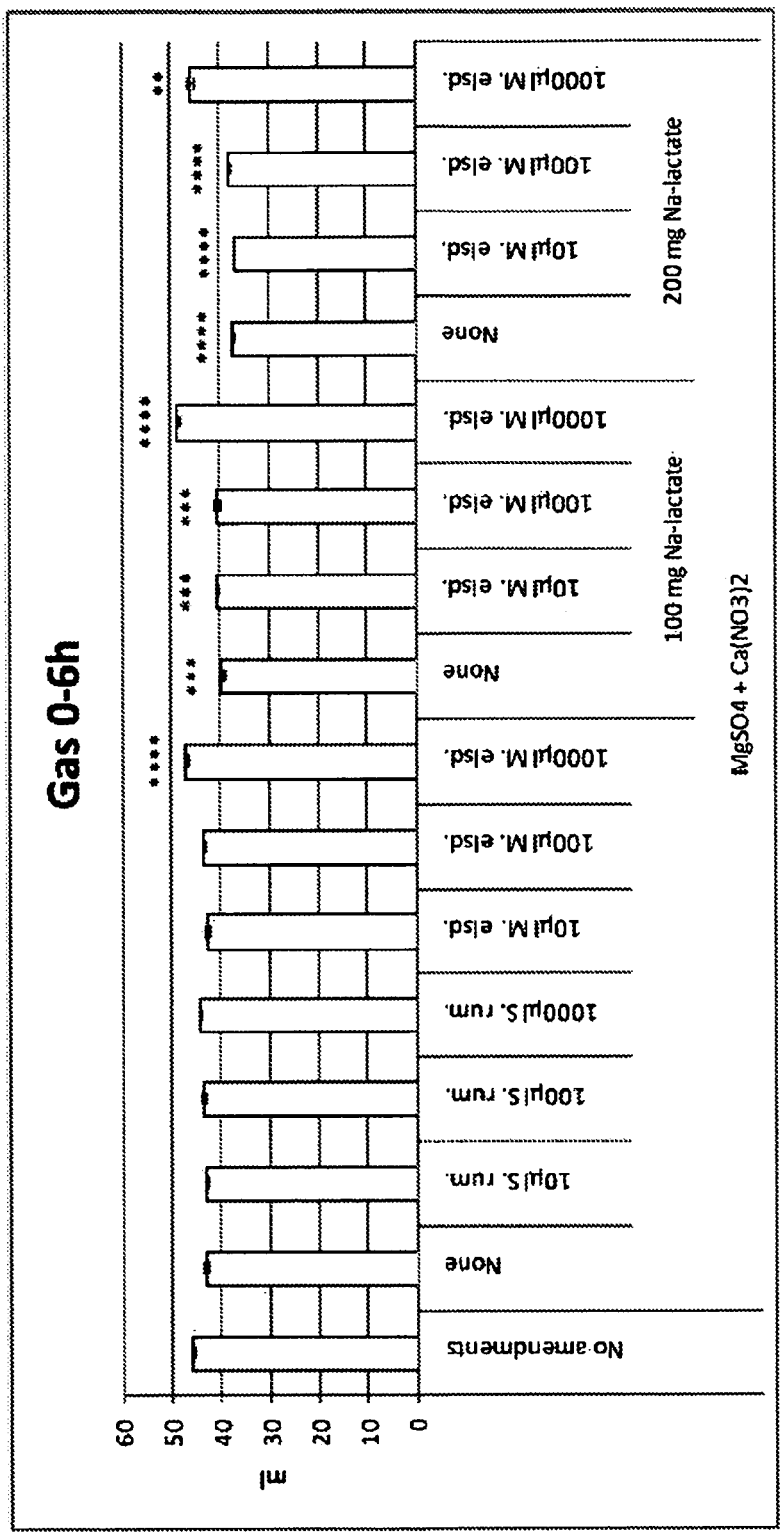
Figure 4C:
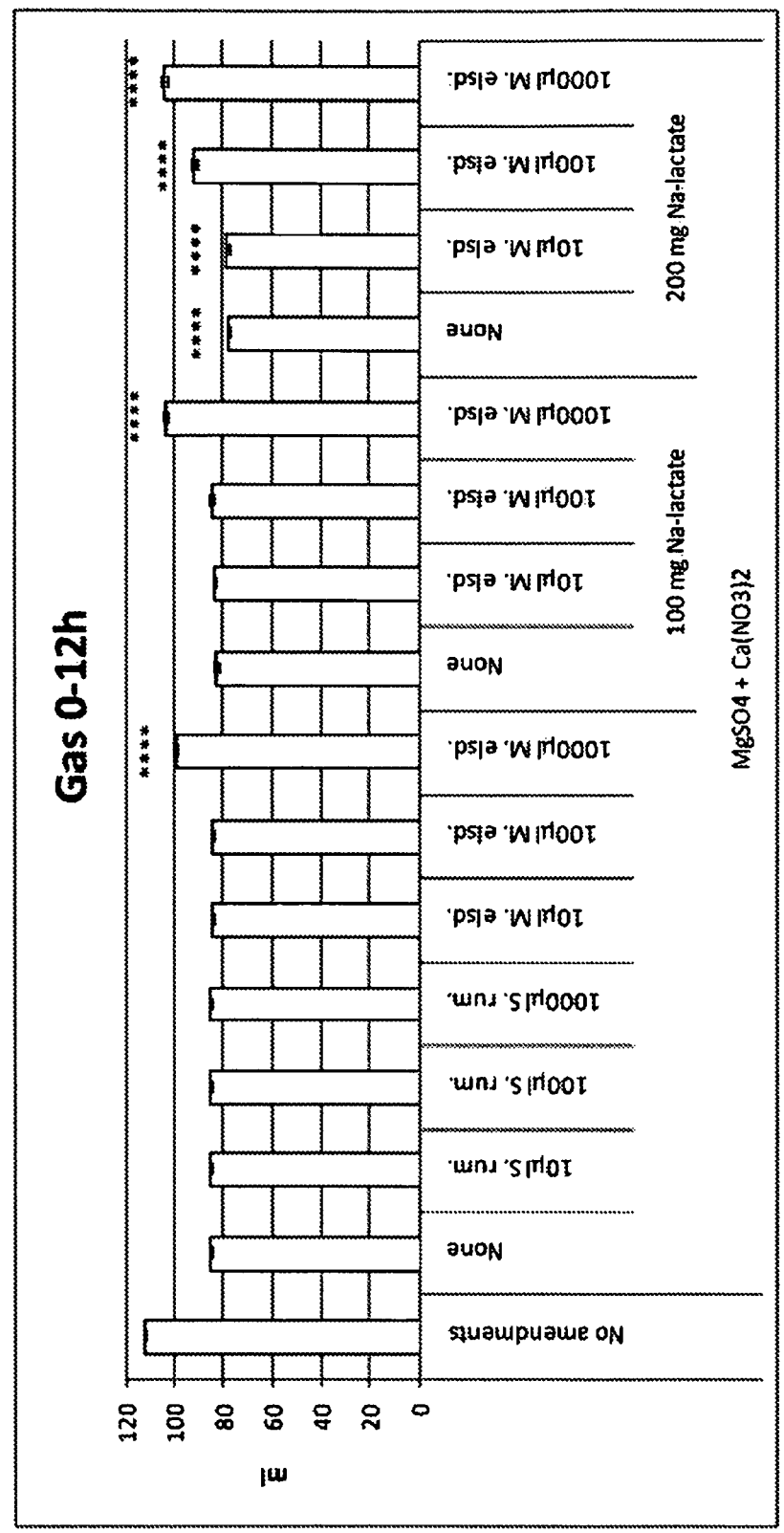

In this work we inoculated all vessels with 5% rumen fluid, but in addition, some vessels received a dose of *Selenomonas ruminantium* or *Megasphaera elsdenii*. These bacteria are the major lactate utilisers in the rumen and, furthermore, it is believed they have a capability to reduce nitrate and/or nitrite. *M. elsdenii* was tested also in combination with lactic acid, the rationale being that lactic acid is a substrate for the bacterium and could have a positive effect on its competitiveness in the rumen microcosm. As shown in FIG. 4 the addition of $NO_3$ and $MgSO_4$ caused significant suppression of gas production. This effect was more pronounced when timed passed; almost 25% suppression of cumulative gas production was measured at 12 h time point.

When compared to the nitrate enriched treatment, *S. ruminantium* inoculum had a positive effect on the gas production during the first 4 hours. This effect was statistically significant at doses 100 and 1000 μl/40 ml. Initial gas production was also stimulated by *M. esdenii*, but only at the highest 1000 μl dose. When lactic acid was provided the gas production was suppressed, which may be due to its direct inhibitory effect on the metabolism of rumen microbiotics. The stimulatory effect of *S. ruminantium* was not detected at the later points of time. However, the highest dose of *M. esldenii* continued to increase cumulative gas production, the relative positive effect being even more significant at the later time points. Lactic acid addition continued to suppress gas production dose dependently for the entire duration of the incubation. However, in combination with lactate the high dose of *M. elsdenii* cancelled the metabolic suppression and, in fact, turned it into stimulation of gas production. Despite the fact that *M. elsdenii* stimulated the overall gas production at high dose, it could not fully overcome the negative effect of nitrate.

Effect of Treatments on Methane Production

Figure 5A:
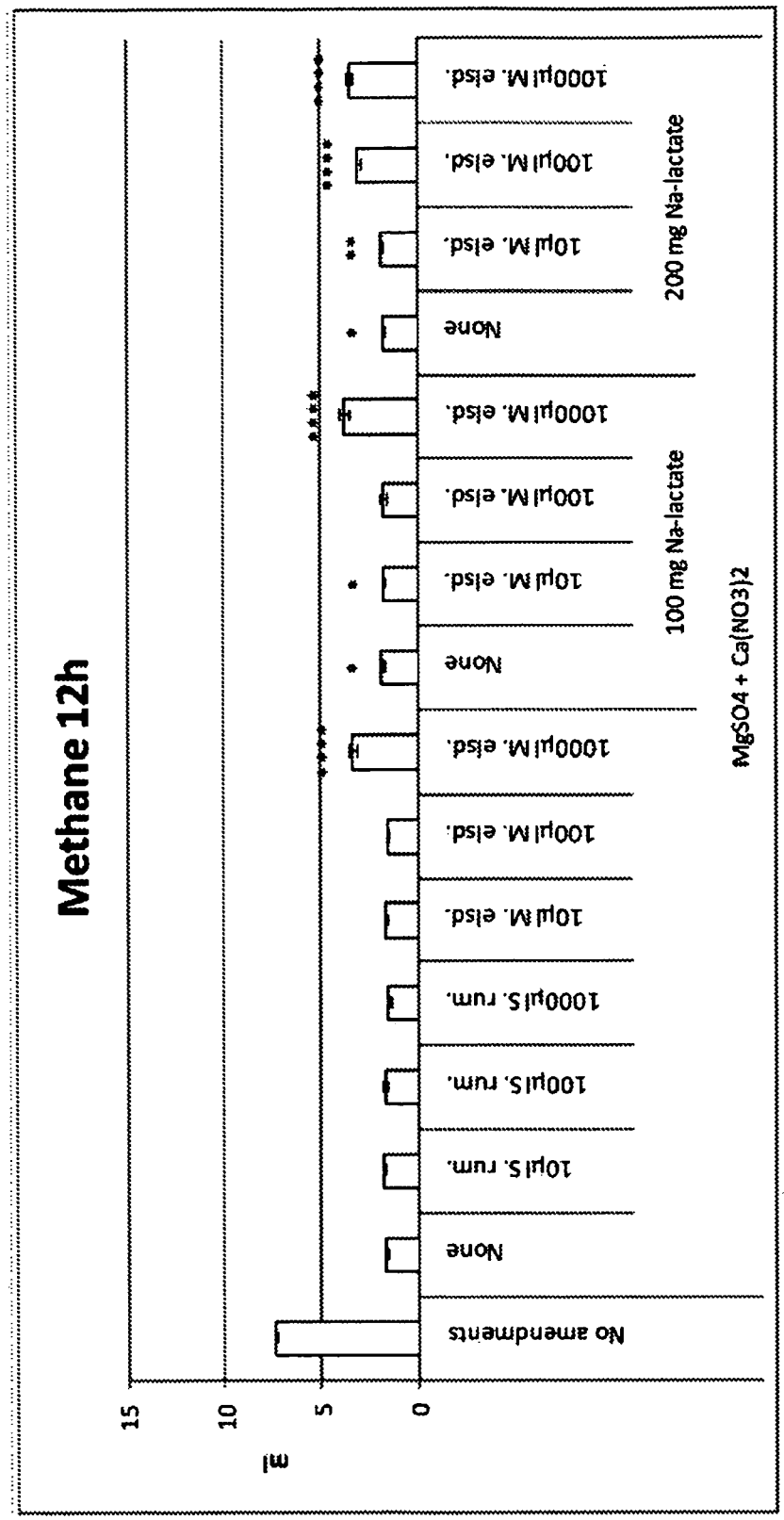
FIG. 5 shows methane production in the rumen simulation with various test products. Panel A shows the cumulative methane production after the 12-hour simulation, and, panel B the proportion of methane in total produced gas. The error bars indicate SE between replicate simulation vessels and asterisks the statistical difference to the Ca(NO3)2+MgSO4 containing control (referred to as "None") with the t-test.
Figure 5B:
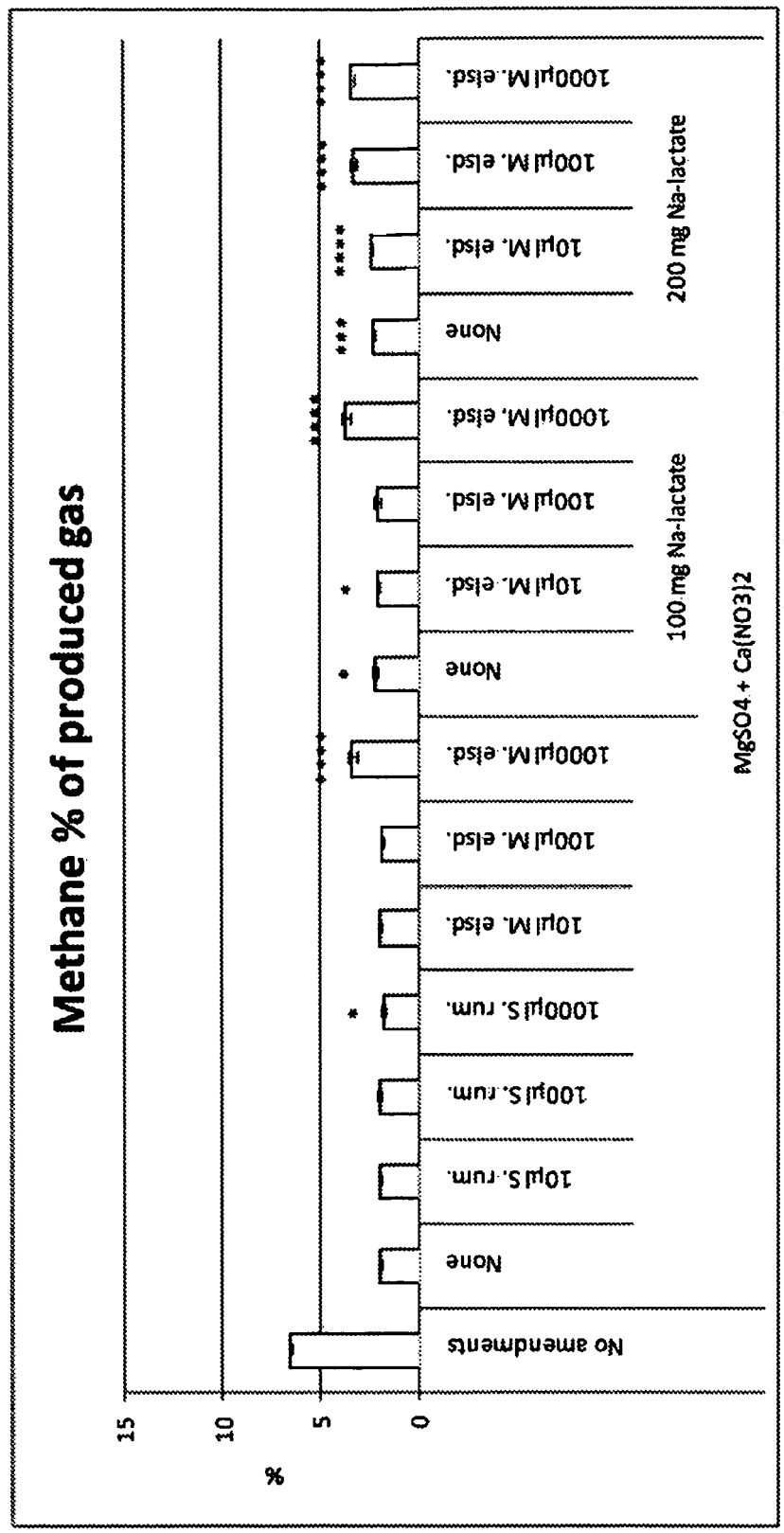

We quantified the produced $CH_4$ in addition to the total gas production. In this fermentation study the proportion of methane of the total produced was relatively low, staying clearly below 10% (FIG. 5B). The level of methane production is dependent on the diet and physiological status of the cow used as a rumen fluid donor. In this case the animal was a milking cow on a high energy diet. Nitrate in the diet suppressed absolute methane production by almost 80% (FIG. 5A).

Effect of Treatments on Nitrate Reduction

Fixed amount of nitrate was added in all simulation vessels, except for those labelled "No amendments", in the form of the product 'Calcinit' (to a final concentration of 14 mM nitrate). In this fermentation study the total produced methane was 7 to 8 ml in the absence of nitrate and it was reduced to 1.5 ml when nitrate was provided.

Figure 6A:
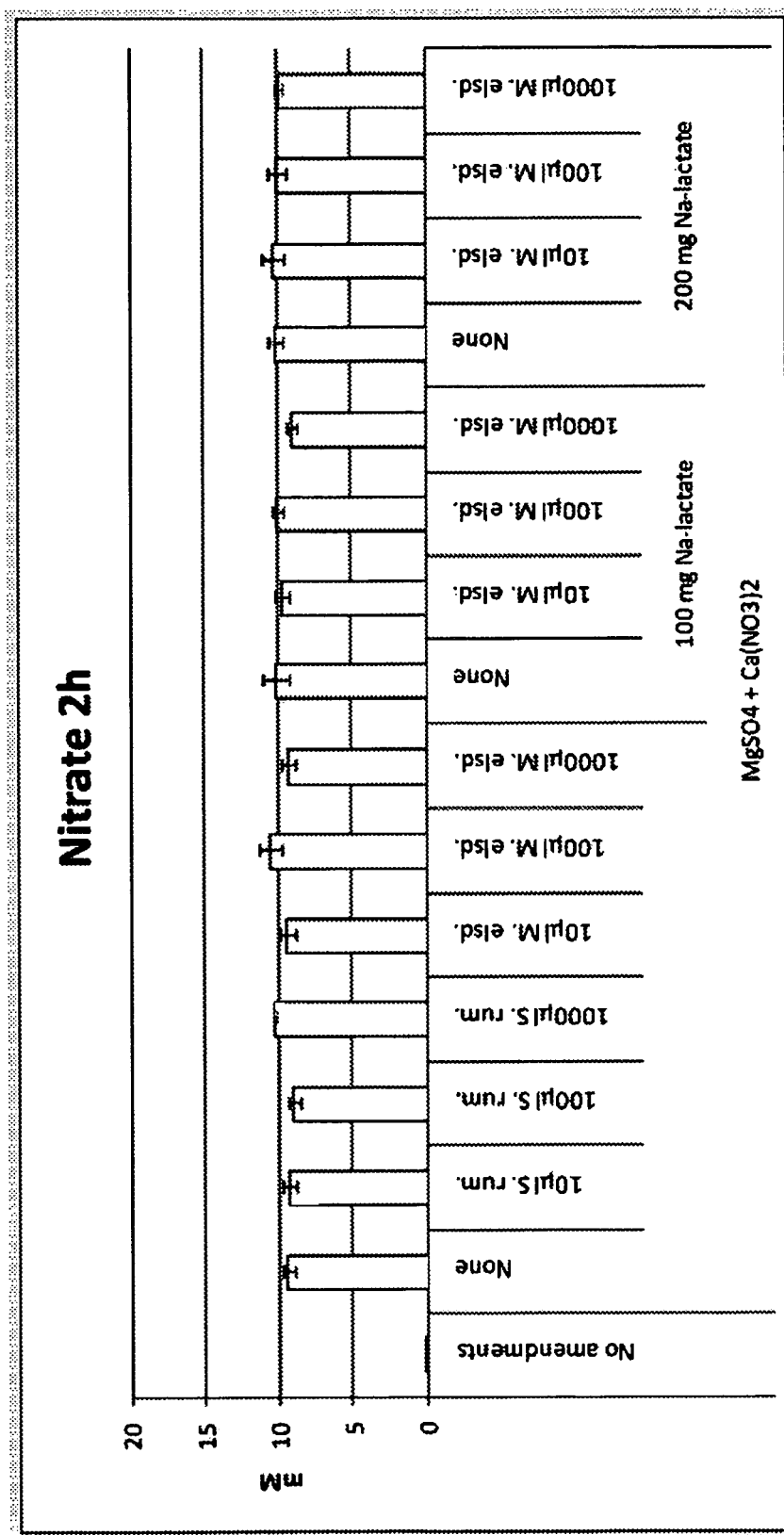
FIG. 6 shows the residual concentration of nitrate in the rumen simulation with various test products. Panels A to C show the residual concentration of nitrate after 2, 4 and 12 hours of fermentation, respectively. The error bars indicate SE between replicate simulation vessels and asterisks the statistical difference to the Ca(NO3)2+MgSO4 containing control (referred to as "None") with the t-test.
Figure 6B:
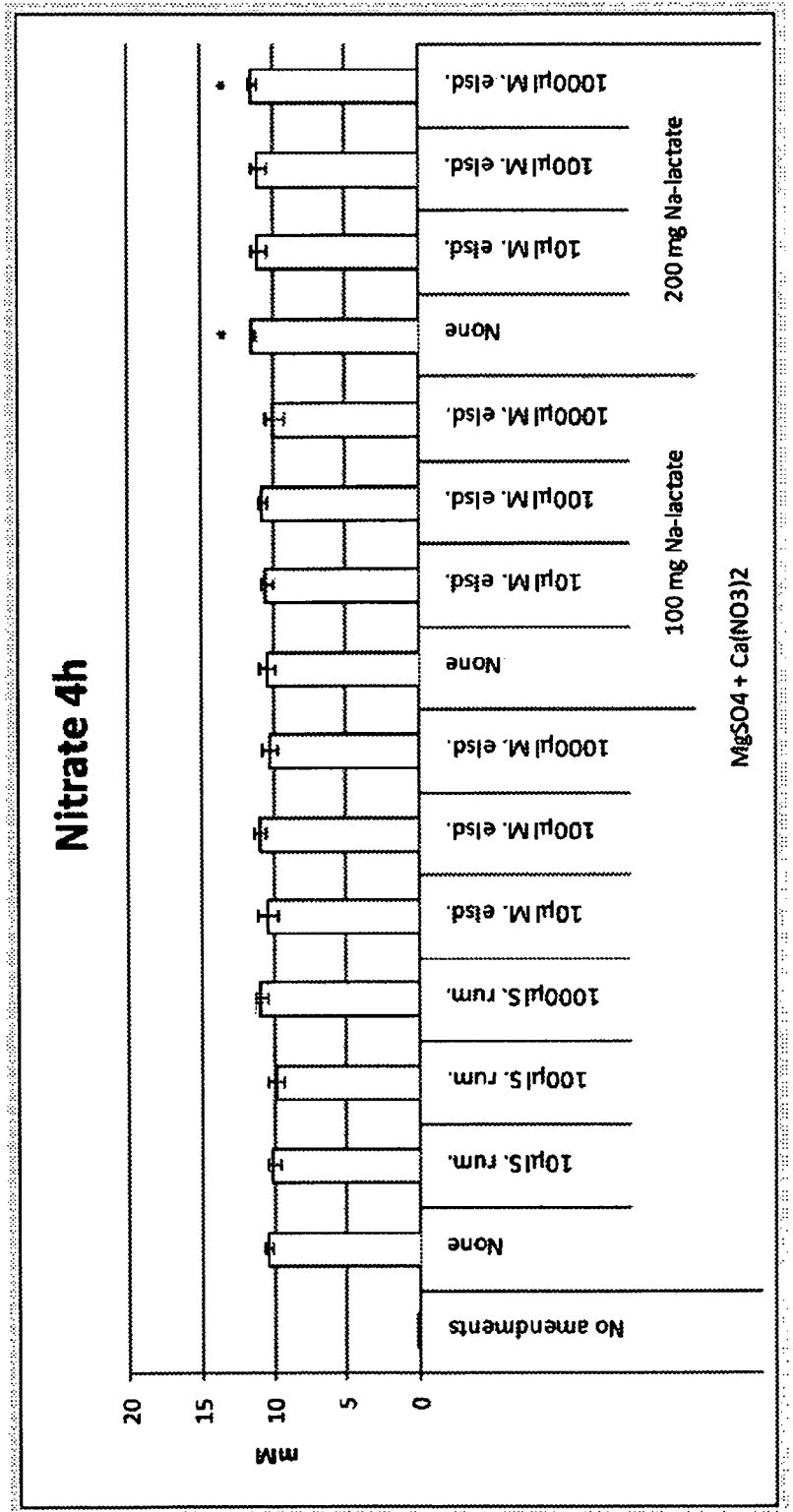

The concentration of nitrate and the products of its reduction, nitrite and ammonium, were analysed after 2, 4 and 12 hours from inoculation. While 14 mM nitrate was provided at 0 hours, only about 10 mM concentration of nitrate was found in the filtrate in all the vessels at 2 hours. Furthermore, the measured nitrate in solution was the same or marginally higher 2 hours later. This suggests that nitrate is rapidly absorbed by the solid matrix or taken up by the microbiota. This equilibrium in partitioning would hold until nitrate consumption by bacteria gets into good speed. In the present study the final sampling indicated a collapse in nitrate level between 4 and 12 hours (FIG. 6). The effect of the high dose of *M. elsdenii* amendment suggested that nitrate reduction was significantly decelerated by the high dose of this bacterium.

Figure 7A:
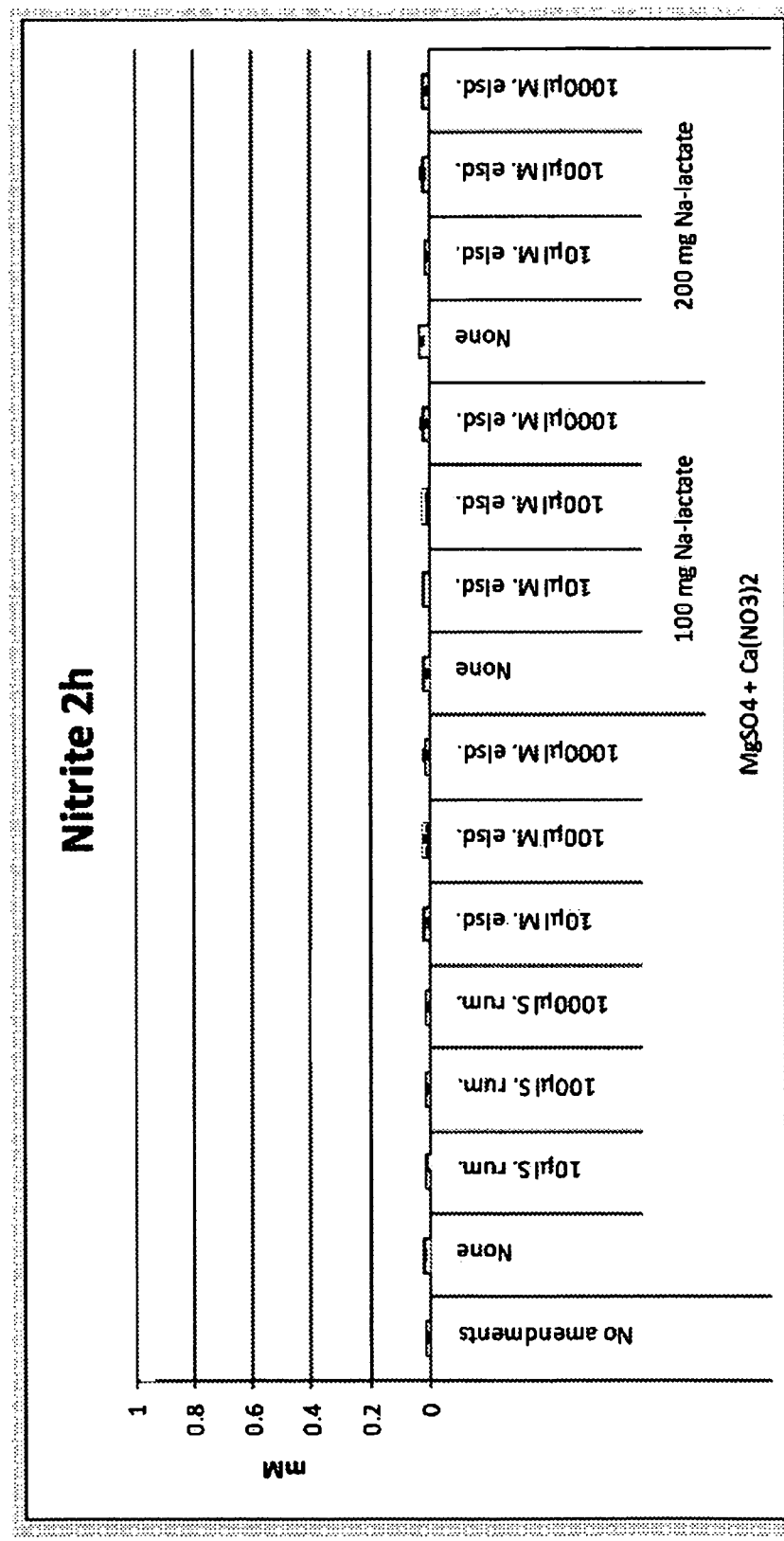
FIG. 7 shows the residual concentration of nitrite in the rumen simulation with various test products. Panels A to C show the residual concentration of nitrite after 2, 4 and 12 hours of fermentation, respectively. The error bars indicate SE between replicate simulation vessels and asterisks the statistical difference to the Ca(NO3)2+MgSO4 containing control (referred to as "None") with the t-test.
Figure 7B:
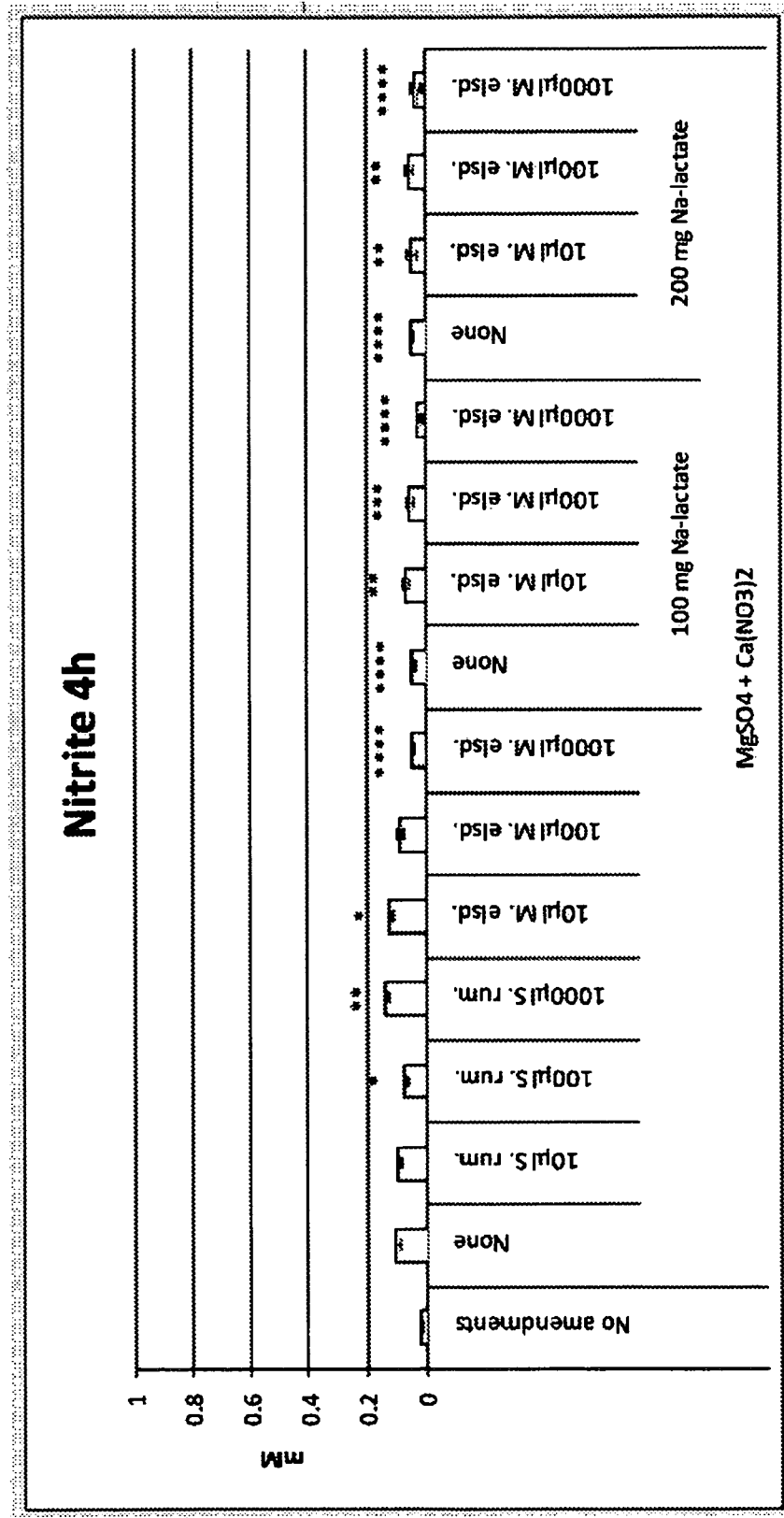
Figure 7C:
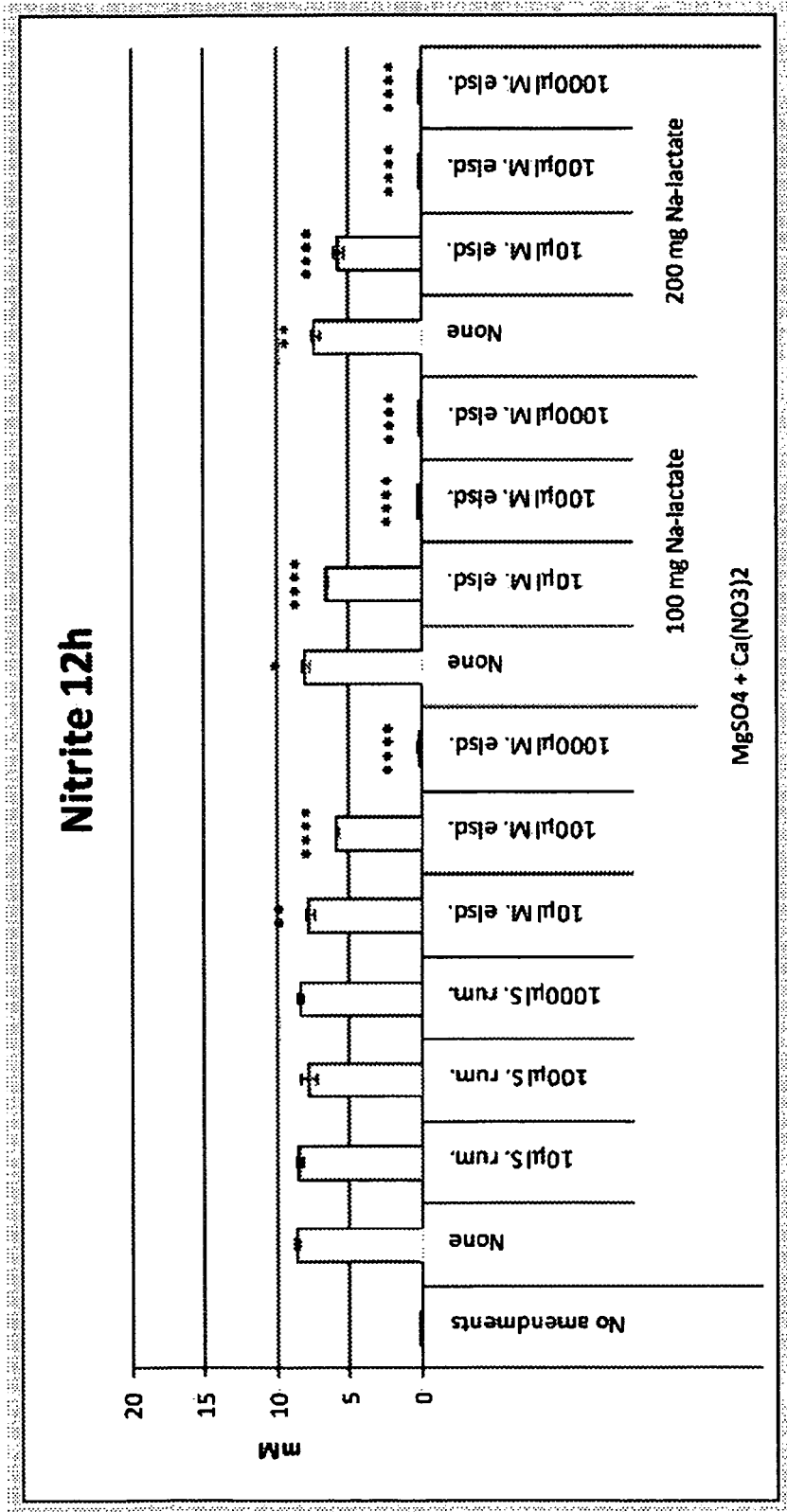

Nitrite analysis at 2 and 4 hour time points was consistent with the nitrate data. At 2 hours the concentration nitrite was below 0.05 mM with all treatments suggesting that the rate of nitrate reduction was low (FIG. 7A). At 4 hours the level of nitrite had started to elevate but was still below 0.2 mM. It is worth noting that while *S. ruminantium* appeared to dose dependently increase nitrite, *M. elsdenii* dose dependently reduced it (FIG. 7B). After 12 hours the effect of *M. elsdenii* was more clear since in its absence the concentration of nitrite had increased to 8 mM and reduced dose dependently when the bacterium was added. With the pure *M. elsdenii* amendment 1000 µl dose was needed to completely remove nitrite. However, when combined with lactate, already 100 µl dose dropped nitrite concentration to the detection limit (FIG. 7C). The nitrite-increasing effect of *S. ruminantium* was no longer detected at 12 hours suggesting that its metabolic role in the microcosm of the rumen model was negligible.

Figure 8A:
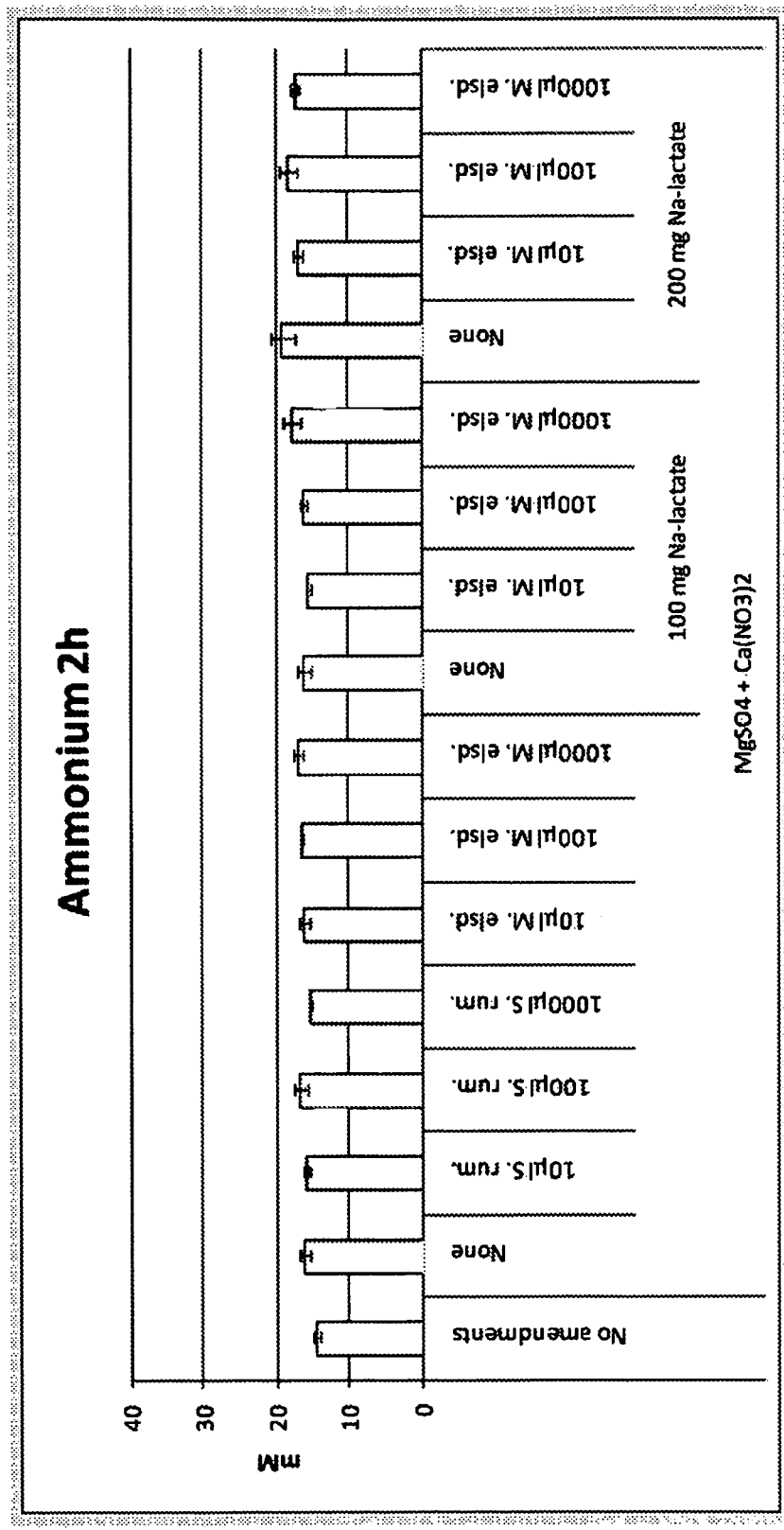
FIG. 8 shows the residual concentration of ammonium in the rumen simulation with various test products. Panels A to C show the residual concentration of ammonium after 2, 4 and 12 hours of fermentation, respectively. The error bars indicate SE between replicate simulation vessels and asterisks the statistical difference to the Ca(NO3)2+MgSO4 containing control (referred to as "None") with the t-test.
Figure 8B:
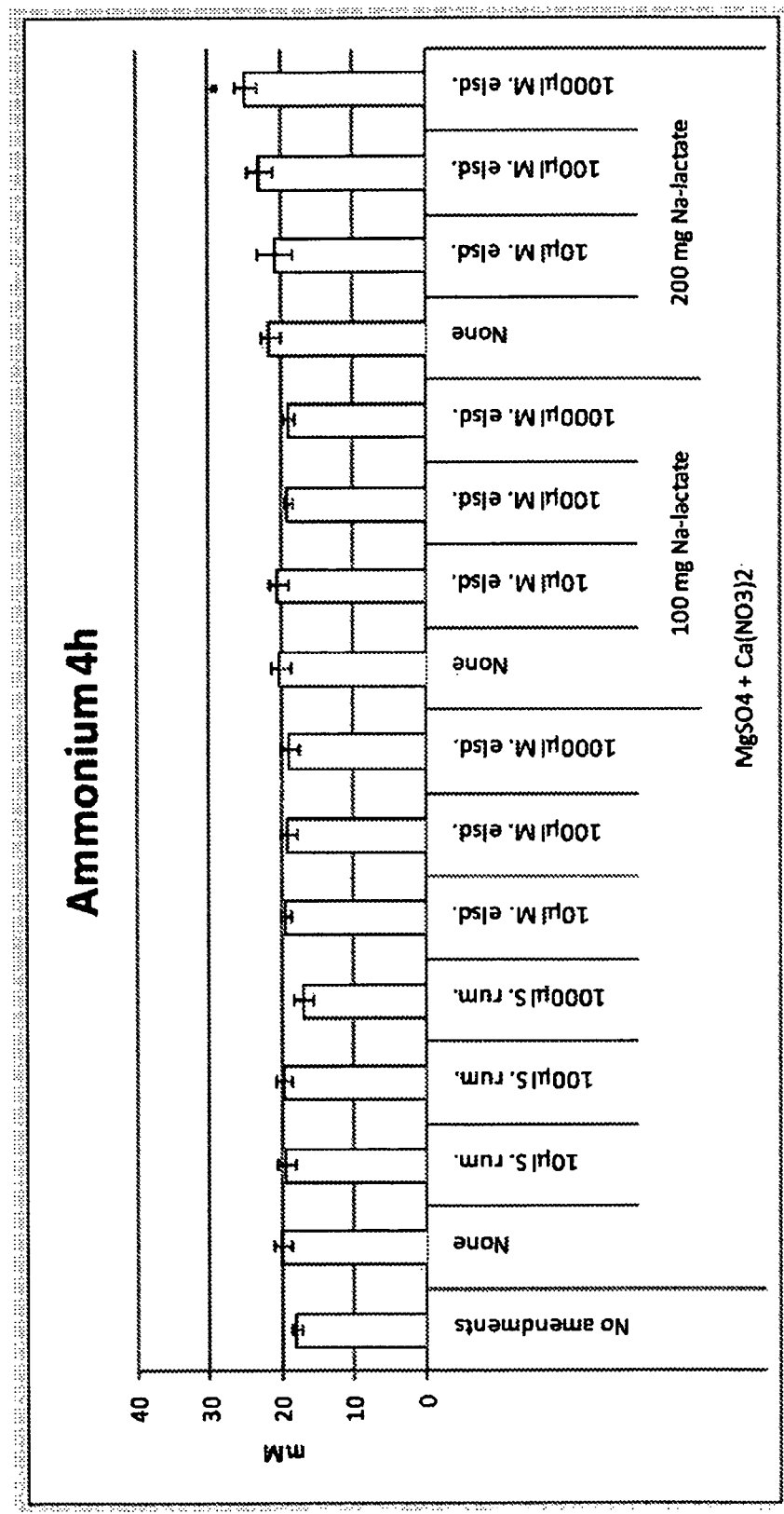
Figure 8C:
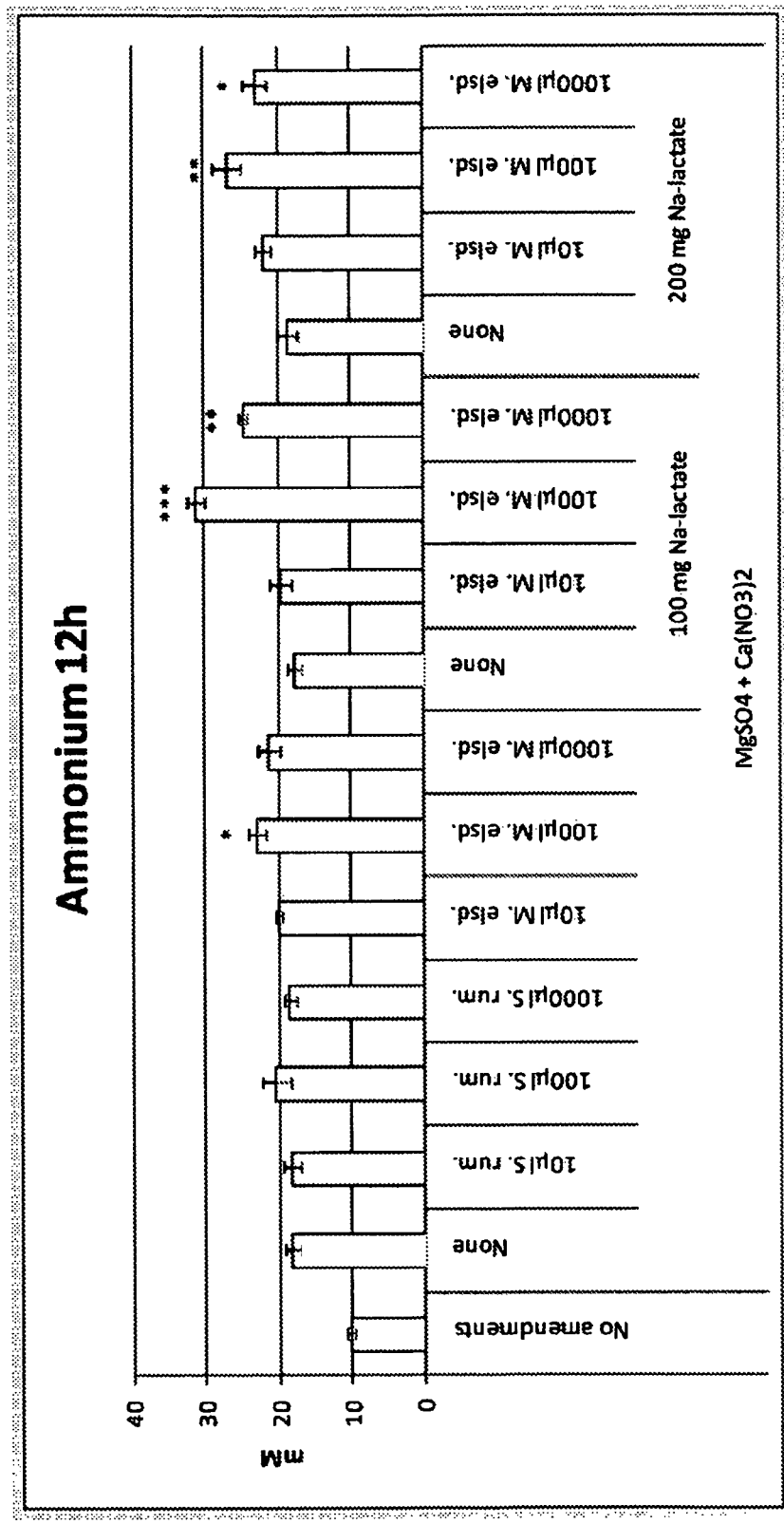

Ammonium is the ultimate reduction product of nitrate/nitrite. However, it is not a product that could be expected to quantitatively accumulate in the microbial system because it is a form of nitrogen that is readily assimilated by microbes when no preferred, organic nitrogen sources are available. This transient role of ammonium makes it impossible to do accurate stoichiometric balance calculations. Still, it was obvious that when 14 mM nitrate was added in the fermentation system the residual concentration of ammonium 12 hours later increased from 10 to 18 mM. When also *M. elsdenii* was added in the fermentation medium the level of ammonium reached 23 to 31 mM concentration depending on the dose of additional lactate substrate provided (FIG. 8C). These data indisputably show that nitrate amendment leads to elevated ammonium production or accumulation. The data also strongly suggest that *M. elsdenii* further strengthens this metabolic process. The residual concentration of ammonium peaked at 100 µl dose of *M. elsdenii*, and, at 1000 µl dose showed a clear decline.

CONCLUSIONS

The data presented here confirmed once again that nitrate in the diet reduces methane production. It also showed that nitrate becomes reduced to nitrite and further to ammonium. This process appeared to be directly linked to methane production since the conditions that prevented quantitative reduction of nitrate also reduced the degree of methanogenesis inhibition.

*M. elsdenii* amendment did not accelerate nitrate reduction but, in fact, appeared to inhibit it. In contrast, the bacterium dose dependently reduced the residual concentration of nitrite and, concomitantly, increased the concentration of its reduction product, ammonium. These data suggest that this strain does not express functional nitrate reductase, but whenever some other bacterium catalyses the reduction of nitrate to nitrite, the strain of *M. elsdenii* readily reduces nitrite further to ammonium. This characteristic makes *M. elsdenii* an ideal preventer of nitrite poisoning resulting from rapid production and accumulation of nitrite by nitrate reducing bacteria.

According to our previous knowledge *M. elsdenii* is not a major lactate utiliser in dairy cows. However, in beef cattle that are being fed high grain diets the conditions for *M. elsdenii* are favourable. The reason is that this very lactate utiliser is highly competitive only when the level of lactic acid in the rumen is high. This characteristic of the bacterium is the reason why we tested here also the effect of lactic acid and the *M. elsdenii*—lactic acid combination. *M. elsdenii* effects on various parameters were to the same direction whether or not lactic acid was included, but when lactic acid was provided the effects were stronger. This suggests that competitiveness of *M. elsdenii* was improved by lactate.

Why did the high dose of *M. elsdenii* inhibit nitrate reduction? This can only be speculated here and the final answer could only come from a specifically designed study. One possible explanation is that, *M. elsdenii* competes for some vital nutrients or cofactors with a major nitrate reducing bacterium. Since the growth of *M. elsdenii* is not dependent on nitrite reduction and outcompetes the nitrate reducer. Another possible explanation is an end product inhibition. High dose of *M. elsdenii* leads to increase in ammonium concentration, which can serve as a feedback inhibitor to nitrate reduction.

REFERENCES

Alaboudi, A. R. and G. A. Jones. 1985. Effect of Acclimation to High Nitrate Intakes on Some Rumen Fermentation Parameters in Sheep. Canadian Journal of Animal Science 65:841-849.

Asanuma, N., M. Iwamoto, and T. Hino. 1999. Effect of the Addition of Fumarate on Methane Production by Ruminal Microorganisms In Vitro. J. Dairy Sci. 82(4):780-787.

Beauchemin, K. A., M. Kieuzer, F. Oâ€™Mara, and T. A. McAllister. 2008. Nutritional management for enteric methane abatement: a review. Australian Journal of Experimental Agriculture 48(2):21-27.

Bruning-Fann, C. S. and J. B. Kaneene. 1993. The effects of nitrate, nitrite, and N-nitroso compounds on animal health. Vet Hum Toxicol 35(3):237-253.

Evelyn, K. A. and H. T. Malloy. 1938. MICRODETERMINATION OF OXYHEMOGLOBIN, METHEMOGLOBIN, AND SULFHEMOGLOBIN IN A SINGLE SAMPLE OF BLOOD journal of biological chemistry 126:655-663.

Guo, W. S., D. M. Schafer, X. X. Guo, L. P. Ren, and Q. X. Meng. 2009. Use of nitrate-nitrogen as a sole dietary nitrogen source to inhibit ruminal methanogenesis and to improve microbial nitrogen synthesis in vitro. Asian-Australian Journal of Animal Science 22(4):542-549.

Iwamoto, M., Asanuma N., and Hino, T. 1999 Effects of nitrate combined with fumarate on methanogenesis, fermentation, and cellulose digestion by mixed ruminal microbes in vitro. Animal Science Journal 70(6):471-478.

Iwamoto, M., Asanuma N., and Hino, T. 2001. Effects of pH and electron donors on nitrate and nitrite reduction in ruminal microbiotica. Animal Science Journal 72(2):117-125.

Joblin, K. N. 1999. Ruminal acetogens and their potential to lower ruminant methane emissions. Australian Journal of Agricultural Research 50(8):1307-1314.

Johnson, K. A. and D. E. Johnson. 1995. Methane emissions from cattle. J Anim Sci 73(8):2483-2492.

Le Van, T. D., J. A. Robinson, J. Ralph, R. C. Greening, W. J. Smolenski, J. A. Z. Leedle, and D. M. Schaefer. 1998. Assessment of Reductive Acetogenesis with Indigenous Ruminal Bacterium Populations and *Acetitomaculum ruminis*. Appl. Environ. Microbiol. 64(9):3429-3436.

Lewis, D. 1951. The metabolism of nitrate and nitrite in the sheep; the reduction of nitrate in the rumen of the sheep. Biochem. J. 48(2):175-170.

Marais, J. P., J. J. Therion, R. I. Mackie, A. Kistner, and C. Dennison. 1988. Effect of nitrate and its reduction products on the growth and activity of the rumen microbial population. British Journal of Nutrition 59(02):301-313.

Molano, G., T. W. Knight, and H. Clark. 2008. Fumaric acid supplements have no effect on methane emissions per unit of feed intake in wether lambs. Australian Journal of Experimental Agriculture 48(2):165-168.

Sar, C., B. Mwenya, B. Santoso, K. Takaura, R. Morikawa, N. Isogai, Y. Asakura, Y. Toride, and J. Takahashi. 2005. Effect of *Escherichia coli* wild type or its derivative with high nitrite reductase activity on in vitro ruminal methanogenesis and nitrate/nitrite reduction. J. Anim Sci. 83(3):644-652.

Sar, C., B. Santoso, B. Mwenya, Y. Gamo, T. Kobayashi, R. Morikawa, K. Kimura, H. Mizukoshi, and J. Takahashi. 2004. Manipulation of rumen methanogenesis by the combination of nitrate with [beta]1-4 galacto-oligosaccharides or nisin in sheep. Animal Feed Science and Technology 115(1-2):129-142.

Steinfeld, H., P. Gerber, T. Wassenaar, V. Castel, M. Rosales, and C. De Haan. 2006. Livestock's Long Shadow. Food and Agriculture Organization of the United Nations. Takahashi, J., M. Ikeda, S. Matsuoka, and H. Fujita. 1998. Prophylactic effect of L-cysteine to acute and subclinical nitrate toxicity in sheep. Animal Feed Science and Technology 74(3):273-280.

Takahashi, J., and Young, B. A. 1991. Prophylactic effect of L-cysteine on nitrate-induced alterations in respiratory exchange and metabolic rate in sheep. Animal Feed Science and Technology 35:105-113.

Takahashi, J., N. Johchi, and H. Fujita. 1989. Inhibitory effects of sulphur compounds, copper and tungsten on nitrate reduction by mixed rumen micro-organisms. British Journal of Nutrition 61(03):741-748.

Ungerfeld, E. M., R. A. Kohn, R. J. Wallace, and C. J. Newbold. 2007. A meta-analysis of fumarate effects on methine production in ruminal batch cultures. J. Anim Sci. 85(10): 2556-2563.

Verstegen, M. W. A., W. Van der Hel, H. A. Brandsma, A. M. Henken, and A. M. Bransen. 1987. The Wageningen respiration unit for animal production research: A description of the equipment and its possibilities. Energy Metabolism in Farm Animals: Effects of Housing, Stress and Disease. Martinus Nijhoff Publishers, Dordrecht, The Netherlands.

The invention claimed is:

1. A non-therapeutic method of reducing gastro-intestinal methane production in a ruminant, said method comprising administering to the ruminant an effective amount of a composition comprising a combination of a nitrate compound and a sulphate compound, wherein the total amount of the combined nitrate and sulphate is in excess of 10 g/kg and less than 750 g/kg.

2. The method according to claim 1, wherein the method increases the efficiency of nutrient use in the ruminant.

3. The method according to claim 1, wherein the method enhances the growth and/or productivity in the ruminant.

4. The method according to claim 1, wherein the combination is administered in an amount providing a total dosage of nitrate and sulphate exceeding 0.05 g/kg body weight per day.

5. The method according to claim 4, wherein the nitrate compound is administered in an amount providing a dosage of nitrate of 0.025-8 g/kg body weight per day and wherein the sulphate compound is administered in an mount providing a dosage of sulphate of 0.025-1.8 g/kg body weight per day.

6. The method according to claim 1, further comprising administering to the ruminant a nitrite-reducing probiotic microorganism in an amount of $1*10^5$-$1*10^{14}$ cfu/kg/day.

7. The method according to claim 6, further comprising administering to the ruminant an effective amount of a lactate compound.

8. A pelletized compounded ruminant animal feed comprising:
a combination of a nitrate compound and a sulphate compound, said combination providing a total amount of nitrate and sulphate in excess of 10 g/kg, wherein the amount of sulphate exceeds 7.5 g/kg on a dry weight basis, wherein the pelletized compounded ruminant animal feed reduces gastrointestinal methane production in a ruminant, and wherein the total amount of the combined nitrate and sulphate is less than 750 g/kg.

9. The compounded animal feed according to claim 8, wherein the amount of nitrate exceeds 7.5 g/kg on a dry weight basis.

10. The compounded animal feed according to claim 8, further comprising a nitrite reducing probiotic microorganism.

11. The compounded animal feed according to claim 10, wherein the nitrite reducing probiotic microorganism is chosen from *Megasphaera elsdenii* and *Propionibacterium acidipropionici*.

12. A ruminant animal feed supplement comprising a combination of a nitrate compound and a sulphate compound, wherein the amount of sulphate in the animal feed supplement, on a dry weight basis, exceeds 25 g/kg and does not exceed 250 g/kg; wherein the total amount of the combined nitrate and sulphate is less than 250 g/kg; wherein the supplement reduces gastrointestinal methane production in a ruminant; and wherein the supplement is in a form chosen from a powder, a compacted solid, and a granulated solid.

* * * * *